United States Patent
Evans et al.

(10) Patent No.: US 10,316,228 B2
(45) Date of Patent: Jun. 11, 2019

(54) MULTI-PHASE SILICONE ACRYLIC HYBRID VISCO-ELASTIC COMPOSITIONS AND METHODS OF MAKING SAME

(71) Applicant: Dow Silicones Corporation, Midland, MI (US)

(72) Inventors: Chana Wilson Evans, Saginaw, MI (US); Robert O. Huber, Midland, MI (US); Linda S. Nartker, Midland, MI (US); Gerald K. Schalau, II, Freeland, MI (US); Xavier Thomas, Famars (FR); Simon Toth, Midland, MI (US)

(73) Assignee: DOW SILICONES CORPORATION, Midland, MI (US)

( * ) Notice: Subject to any disclaimer, the term of this patent is extended or adjusted under 35 U.S.C. 154(b) by 3 days.

(21) Appl. No.: 15/545,133

(22) PCT Filed: Feb. 5, 2016

(86) PCT No.: PCT/US2016/016674
§ 371 (c)(1),
(2) Date: Jul. 20, 2017

(87) PCT Pub. No.: WO2016/130408
PCT Pub. Date: Aug. 18, 2016

(65) Prior Publication Data
US 2018/0002583 A1    Jan. 4, 2018

Related U.S. Application Data

(60) Provisional application No. 62/113,815, filed on Feb. 9, 2015.

(51) Int. Cl.
| | | |
|---|---|---|
| C09J 183/10 | (2006.01) |
| C08G 77/20 | (2006.01) |
| C08G 77/442 | (2006.01) |
| A61K 9/70 | (2006.01) |
| A61K 31/167 | (2006.01) |
| A61K 31/192 | (2006.01) |
| A61K 31/565 | (2006.01) |
| C08F 290/06 | (2006.01) |
| C09J 7/38 | (2018.01) |
| C09J 155/00 | (2006.01) |

(52) U.S. Cl.
CPC .......... *C09J 183/10* (2013.01); *A61K 9/7023* (2013.01); *A61K 9/7069* (2013.01); *A61K 31/167* (2013.01); *A61K 31/192* (2013.01); *A61K 31/565* (2013.01); *C08F 290/068* (2013.01); *C08G 77/20* (2013.01); *C08G 77/442* (2013.01); *C09J 7/38* (2018.01); *C09J 155/005* (2013.01); *C09J 2433/00* (2013.01); *C09J 2483/00* (2013.01)

(58) Field of Classification Search
CPC .................................................... C08G 77/442
See application file for complete search history.

(56) References Cited

U.S. PATENT DOCUMENTS

| | | | | |
|---|---|---|---|---|
| 8,614,278 B2 * | 12/2013 | Loubert | ............... | A61K 9/7084 424/443 |
| 2002/0004065 A1 | 1/2002 | Kanios | | |
| 2009/0196911 A1 | 8/2009 | Loubert et al. | | |
| 2012/0108560 A1 | 3/2012 | Evans et al. | | |
| 2012/0095159 A1 | 4/2012 | Liu et al. | | |
| 2012/0114737 A1 | 10/2012 | Loubert et al. | | |
| 2013/0012653 A1 | 1/2013 | Liu | | |
| 2015/0182383 A1 | 7/2015 | Carty et al. | | |

FOREIGN PATENT DOCUMENTS

EP    2584016    4/2013

OTHER PUBLICATIONS

Odian, George Chapter 3 of Principles of Polymerization, Fourth Edition, Wiley-Interscience, 2004, New Jersey.
Satas, Donatas Chapter 19 of the Handbook of Pressure Sensitive Adhesive Technology, Third Edition, Satas & Associates, 1999, Warwick, R.I.

* cited by examiner

Primary Examiner — Kuo Liang Peng
(74) Attorney, Agent, or Firm — Matthew T. Fewkes

(57) ABSTRACT

A multi-phase silicone acrylic hybrid visco-elastic composition prepared by polymerizing an ethylenically unsaturated monomer and a silicon-containing pressure sensitive adhesive composition comprising acrylate or methacrylate functionality in a first solvent in the presence of an initiator, removing the first solvent, and adding a second solvent to form the multi-phase silicone acrylic hybrid visco-elastic composition. Alternatively, a multi-phase silicone acrylic hybrid visco-elastic composition prepared by polymerizing an ethylenically unsaturated monomer and a silicon-containing pressure sensitive adhesive composition comprising acrylate or methacrylate functionality in a first solvent in the presence of an initiator, adding a processing solvent having a higher boiling point than the first solvent, applying heat to selectively remove a majority of the first solvent, removing the processing solvent, and adding a second solvent to form the multi-phase silicone acrylic hybrid visco-elastic composition. The phase arrangement of the multi-phase silicone acrylic hybrid visco-elastic compositions is selectively controlled by selection of the second solvent.

18 Claims, 5 Drawing Sheets

MULTI-PHASE SILICONE ACRYLIC HYBRID VISCO-ELASTIC COMPOSITIONS AND METHODS OF MAKING SAME

CROSS REFERENCE TO RELATED APPLICATIONS

This application is a U.S. national stage filing under 35 U.S.C. § 371 of PCT Application No. PCT/US16/016674 filed on 5 Feb. 2016, which claims the benefit of U.S. Provisional Patent Application No. 62/113,815 filed 9 Feb. 2015 under 35 U.S.C. § 119 (e). PCT Application No. PCT/US16/016674 and U.S. Provisional Patent Application No. 62/113,815 are hereby incorporated by reference.

BRIEF SUMMARY OF THE INVENTION

The present invention generally relates to a multi-phase silicone acrylic hybrid visco-elastic composition and a method of making the multi-phase silicone acrylic hybrid visco-elastic composition. More specifically, the present invention relates to a multi-phase silicone acrylic hybrid visco-elastic composition that is prepared by polymerizing an ethylenically unsaturated monomer and a silicon-containing pressure sensitive adhesive composition comprising acrylate or methacrylate functionality in a first solvent in the presence of an initiator to form a silicone acrylic hybrid composition, removing the first solvent, and adding a second solvent to form the multi-phase silicone acrylic hybrid visco-elastic composition. The present invention alternatively relates to a multi-phase silicone acrylic hybrid visco-elastic composition that is prepared by polymerizing an ethylenically unsaturated monomer and a silicon-containing pressure sensitive adhesive composition comprising acrylate or methacrylate functionality in a first solvent in the presence of an initiator to form a silicone acrylic hybrid composition, adding a processing solvent having a higher boiling point than the first solvent, applying heat to selectively remove a majority of the first solvent, removing the processing solvent; and adding a second solvent to form the multi-phase silicone acrylic hybrid visco-elastic composition. The phase arrangement of the multi-phase silicone acrylic hybrid visco-elastic compositions is selectively controlled by selection of the second solvent. The present invention also relates to the multi-phase silicone acrylic hybrid visco-elastic compositions formed by these processes.

BRIEF DESCRIPTION OF THE DRAWINGS

Various advantages of the invention will become apparent upon reading the following detailed description and upon reference to the drawings.

Figure 1:
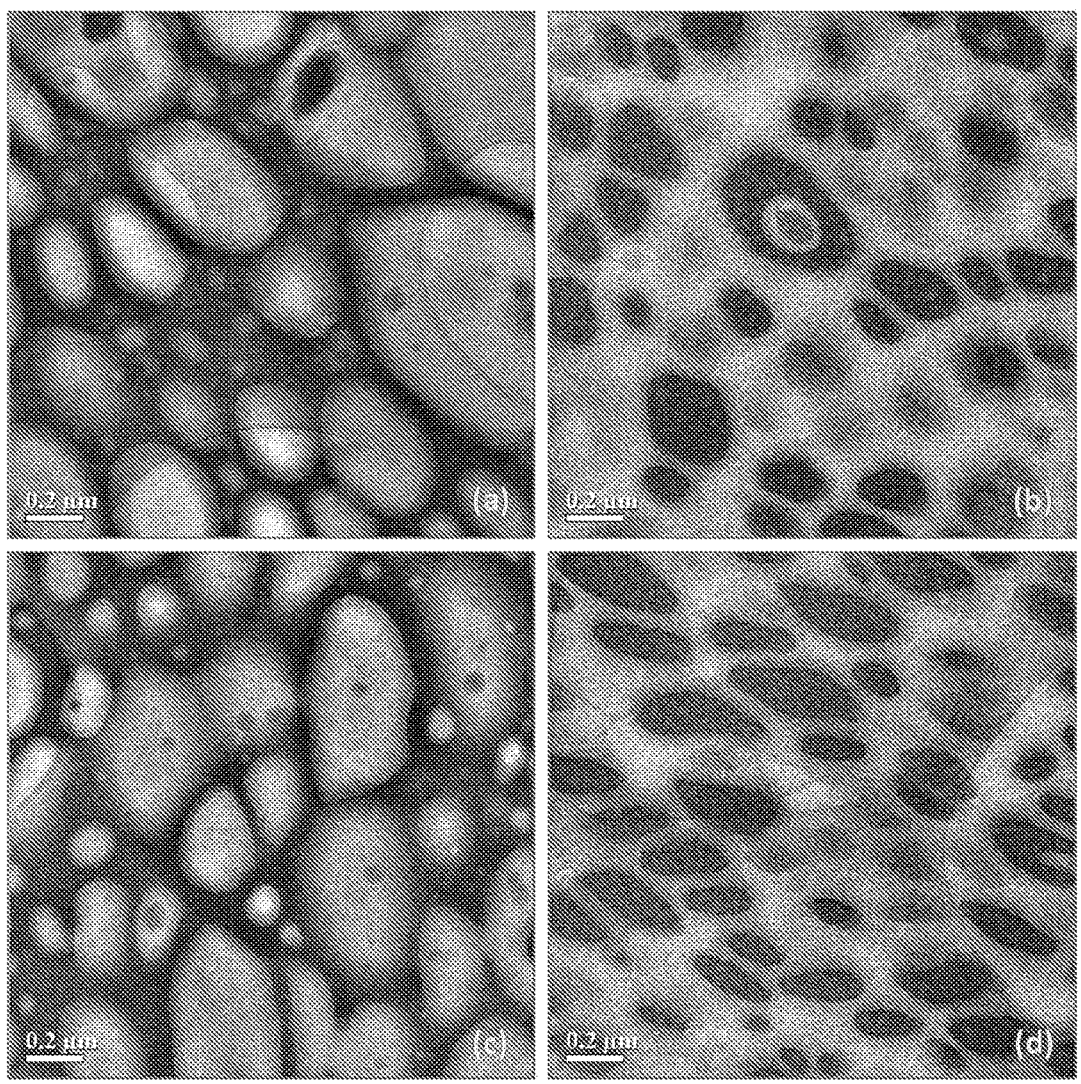
FIG. 1 is a transmission electron micrograph of a high tack, hybrid visco-elastic polymer film dried from a multi-phase silicone acrylic hybrid visco-elastic composition polymerized in ethyl acetate and dispersed in heptane (a) and ethyl acetate (b) and a low tack hybrid visco-elastic polymer film dried from a multi-phase silicone acrylic hybrid visco-elastic composition polymerized in ethyl acetate and dispersed in heptane (c) and ethyl acetate (d). The light color in the micrographs corresponds to the acrylate phase and the dark color corresponds to the silicone phase.

While the invention is susceptible to various modifications and alternative forms, specific embodiments have been shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention.

DETAILED DESCRIPTION OF THE INVENTION

The present invention relates to a multi-phase silicone acrylic hybrid visco-elastic composition that is prepared by (i) providing a silicon-containing pressure sensitive adhesive composition comprising acrylate or methacrylate functionality, (ii) polymerizing an ethylenically unsaturated monomer and the silicon-containing pressure sensitive adhesive composition in a first solvent in the presence of an initiator to form a silicone acrylic hybrid composition, (iii) removing the first solvent, and (iv) adding a second solvent to form the multi-phase silicone acrylic hybrid visco-elastic composition. The phase arrangement of the multi-phase silicone acrylic hybrid visco-elastic composition is selectively controlled by selection of the second solvent. This embodiment of the present invention is referred to in the subject description as Embodiment One of the present invention. The method of Embodiment One of the present invention optionally further includes the step of blending the silicone acrylic hybrid composition from step (ii) with a non-hybrid pressure sensitive adhesive composition prior to step (iii), wherein the phase arrangement of the multi-phase silicone acrylic hybrid visco-elastic composition is selectively controlled by the blending step. Alternatively and preferably, the method of Embodiment One of the present invention optionally further includes the step of blending the multi-phase silicone acrylic hybrid visco-elastic composition with a non-hybrid pressure sensitive adhesive composition after step (iv), wherein the phase arrangement of the multi-phase silicone acrylic hybrid visco-elastic composition is selectively controlled by the blending step. The present invention also relates to the multi-phase silicone acrylic hybrid visco-elastic composition formed by this process.

In an alternative embodiment, the present invention relates to a multi-phase silicone acrylic hybrid visco-elastic composition that is prepared by (i) providing a silicon-containing pressure sensitive adhesive composition comprising acrylate or methacrylate functionality, (ii) polymerizing an ethylenically unsaturated monomer and the silicon-containing pressure sensitive adhesive composition in a first solvent in the presence of an initiator to form a silicone acrylic hybrid composition, (iii) adding a processing solvent, where the processing solvent has a higher boiling point than the first solvent, (iv) applying heat such that a majority of the first solvent is selectively removed, (v) removing the processing solvent, and (vi) adding a second solvent to form the multi-phase silicone acrylic hybrid visco-elastic composition. The phase arrangement of the multi-phase silicone acrylic hybrid visco-elastic composition is selectively controlled by selection of the second solvent. This alternative embodiment of the present invention is referred to in the subject description as Embodiment Two of the present invention. The method of Embodiment Two of the present invention optionally further includes the step of blending the silicone acrylic hybrid composition from step (ii) with a non-hybrid pressure sensitive adhesive composition prior to step (iii), wherein the phase arrangement of the multi-phase silicone acrylic hybrid visco-elastic composition is selectively controlled by the blending step. Alternatively and preferably, the method of Embodiment Two of the present invention optionally further includes the step of blending the multi-phase silicone acrylic hybrid visco-elastic composition with a non-hybrid pressure sensitive adhesive composition after step (vi), wherein the phase arrangement of the multi-phase silicone acrylic hybrid visco-elastic composition is selectively controlled by the blending step. The present invention also relates to the multi-phase silicone acrylic hybrid visco-elastic composition formed by this process.

As used herein, the term "hybrid composition" refers to a composition comprised of two distinct chemistry sets which are polymerized together and is intended to denote more than a simple blend of the two sub-species. As used herein, the term "silicone acrylic hybrid" refers to a hybrid composition comprised of two distinct chemistry sets wherein the two distinct chemistry sets are silicone and polyacrylate. As used herein, the term "non-hybrid pressure sensitive adhesive composition" refers to a pressure sensitive adhesive that is composed of only one chemistry set, typically silicone or acrylate. As used herein, the term "visco-elastic" refers to the property of possessing both viscous and elastic characteristics when undergoing deformation and exhibiting time-dependent strain. As used herein, the term "multi-phase" refers to having or containing more than one phase. This property is characterized as having a primary or continuous phase with domains or droplets of at least one other phase suspended within the continuous phase. As used herein, the term "dispersion" refers to a system in which one material is dispersed in a different material, but not solubilized as it would be in a solution. As used herein, the term "silicon-containing pressure sensitive adhesive composition" refers to the condensation product of a hydroxy end-blocked polydimethylsiloxane and a trimethylsiloxy-hydroxy end-blocked silicate resin solution.

The processes of the present invention facilitate the phase arrangement of the resulting multi-phase silicone acrylic hybrid visco-elastic composition to be selectively controlled. Depending on the selection of the second solvent, the resulting multi-phase silicone acrylic hybrid visco-elastic composition contains (1) a continuous, silicone external phase and a discontinuous, acrylic internal phase or (2) a continuous, acrylic external phase and a discontinuous, silicone internal phase as selectively controlled by selection of the second solvent. In other words, acrylic domains dispersed in a continuous, silicone external phase or silicone domains dispersed in a continuous, acrylic external phase can be achieved as desired as selectively controlled by selection of the second solvent using the methods described herein. These arrangements are achieved by the presence of linkages between the silicone and acrylate polymers.

The physiochemical properties of the multi-phase silicone acrylic hybrid visco-elastic composition are affected by which phase is external and which phase is internal. Furthermore, the drug release properties of the multi-phase silicone acrylic hybrid visco-elastic composition are also affected by which phase is external and which phase is internal. The methods of the present invention facilitate the ability to control, adjust or tune the physiochemical and drug release properties of the multi-phase silicone acrylic hybrid visco-elastic compositions based on what phase or domain arrangement is achieved.

The Silicon-Containing Pressure Sensitive Adhesive Composition

The silicon-containing pressure sensitive adhesive compositions used in the present invention comprise acrylate or methacrylate functionality. It is to be understood that the silicon-containing pressure sensitive adhesive compositions can include only acrylate functionality, only methacrylate functionality, or both acrylate functionality and methacrylate functionality. The silicon-containing pressure sensitive adhesive composition is preferably present in the silicone acrylic hybrid composition in an amount of from about 5 to about 95, more preferably about 25 to 75, and still more preferably about 40 to 60 parts by weight based on 100 parts by weight of the silicone acrylic hybrid composition.

Desirably, the silicon-containing pressure sensitive adhesive compositions used in the present invention comprise the condensation reaction product of a pressure sensitive adhesive and a silicon-containing capping agent. As explained additionally below, the silicon-containing capping agent provides the acrylate or methacrylate functionality to the silicon-containing pressure sensitive adhesive composition. It is to be understood that, in the context of the description of the present invention, the term "pressure sensitive adhesive" is distinguishable from the term "silicon-containing pressure sensitive adhesive composition". The silicon-containing pressure sensitive adhesive composition, as described herein, is preferably the reaction product of the pressure sensitive adhesive and a silicon-containing capping agent. That is, the silicon-containing pressure sensitive adhesive composition is essentially a pressure sensitive adhesive that has been capped or endblocked with the capping agent or agents described herein. The capping agent and the pressure sensitive adhesive react to form the silicon-containing pressure sensitive adhesive composition.

The silicon-containing pressure sensitive adhesive composition preferably comprises the condensation reaction product of a silicone resin and a silicone polymer. Preferably, the silicone resin reacts in an amount of from 30 to 80 parts by weight to form the pressure sensitive adhesive, and the silicone polymer reacts in an amount of from 20 to 70 parts by weight to form the pressure sensitive adhesive. Both of these parts by weight are based on 100 parts by weight of the pressure sensitive adhesive. Although not required, the pressure sensitive adhesive may comprise a catalytic amount of a condensation catalyst. A wide array of silicone resins and silicone polymers are suitable to make up the pressure sensitive adhesive.

A preferred silicone resin for use in embodiments of the invention comprises a copolymer comprising triorganosiloxy units of the formula $R^3_3SiO_{1/2}$ and tetrafunctional siloxy units of the formula $SiO_{4/2}$ in a ratio of about 0.6 to 0.9 triorganosiloxy units for each tetrafunctional siloxy unit, wherein each $R^3$ independently denotes a monovalent hydrocarbon radical having from 1 to 6 carbon atoms, and a preferred silicone polymer comprises at least one polydiorganosiloxane comprising $AR^3SiO$ units terminated with endblocking $TR^3ASiO1/2$ units, wherein the poly-diorganosiloxane has a viscosity of from about 100 centipoise to about 30,000,000 centipoise at 25° C., each A radical is independently selected from $R^3$ or halohydro-carbon radicals having from 1 to 6 carbon atoms, each T radical is independently selected from the group consisting of $R^3$, OH, H or $OR^4$, and each $R^4$ is independently an alkyl radical having from 1 to 4 carbon atoms.

As alluded to above, the pressure sensitive adhesive of the embodiments of the invention comprises a concentration of silicon bonded hydroxyl groups (i.e., silanols) and the silicon-containing capping agent is further defined as an endblocking agent. Once again, the terms end-blocking agents and capping agents are used interchangeably throughout the art and in the subject description. The end-blocking agent and the pressure sensitive adhesive are condensed to produce the silicon-containing pressure sensitive adhesive composition. More specifically, the endblocking agent reacts with the concentration of silicon bonded hydroxyl groups to cap the pressure sensitive adhesive. As generally alluded to above, once the endblocking agent reacts with the pressure sensitive adhesive, the concentration of silanols in the composition is from 5,000 to 15,000, more typically from 8,000 to 13,000, ppm.

Although not required, the pressure sensitive adhesive is preferably present in the silicon-containing pressure sensitive adhesive composition in an amount of from 85.0 to 99.9 parts by weight based on weight % solids of the pressure sensitive adhesive, and the silicon-containing capping agent is preferably present in the silicon-containing pressure sensitive adhesive composition in an amount of from 0.1 to 15 parts by weight based on weight % solids of the pressure sensitive adhesive. More preferably, the pressure sensitive adhesive is present in the silicon-containing pressure sensitive adhesive composition in an amount of from 90.0 to 99.9 parts by weight based on weight % solids of the pressure sensitive adhesive, and the silicon-containing capping agent is preferably present in the silicon-containing pressure sensitive adhesive composition in an amount of from 0.05 to 10 parts by weight based on weight % solids of the pressure sensitive adhesive. Typically, the pressure sensitive adhesive has a weight % solids of from 50 to 65%, more typically 60%.

In the embodiments of the invention, the endblocking agent can be introduced to react with the pressure sensitive adhesive after the pressure sensitive adhesive has already been formed, i.e., after the silicone resin and the silicone polymer which make up the pressure sensitive adhesive have reacted. In this case, the silicon-containing capping agent reacts with the pressure sensitive adhesive after the silicone resin and the silicone polymer have been condensation reacted to form the pressure sensitive adhesive.

Alternatively, the endblocking agent can be reacted in situ with the silicone resin and the silicone polymer such that the endblocking agent is present as the silicone resin and the silicone polymer are reacting. That is, in this in situ scenario, the endblocking agent is introduced either prior to or during the reaction of the silicone resin and the silicone polymer. In any event, in this in situ scenario, the silicone resin and the silicone polymer are reacted in the presence of the silicon-containing capping agent, and the silicon-containing capping agent is reacted in situ with the silicone resin and the silicone polymer as the silicone resin and the silicone polymer are condensation reacting to form the pressure sensitive adhesive.

In one preferred embodiment of the present invention, the silicon-containing capping agent is selected from the group of acrylate functional silanes, acrylate functional silazanes, acrylate functional disilazanes, acrylate functional disiloxanes, methacrylate functional silanes, methacrylate functional silazanes, methacrylate functional disilazanes, methacrylate functional disiloxanes, and combinations thereof.

Alternatively, the endblocking agent used in in embodiments of the invention may be described to be of the general formula $(XYR_2Si)2D$ wherein X is a monovalent radical of the general formula AE- where E is —O— or —NH— and A is an acryl group or a methacryl group, Y is a divalent alkylene radical having from 1 to 6 carbon atoms, R is a methyl or a phenyl radical, and D is a divalent or a trivalent organic hydrolyzable radical. Preferably, D is —O— or —NH—. Most preferably, this particular endblocking agent is selected from the group of Bis(3-methacryloxypropyl) tetramethyldisilazane, Bis(3-acryloxypropyl)tetramethyldisilazane, Bis(3-methacryloxypropyl)tetramethyldisiloxane, Bis(3-acryloxypropyl) tetramethyldisiloxane, and combinations thereof.

The acryl group provides the silicon-containing capping agent with acrylate functionality and the methacryl group provides the silicon-containing capping agent with the methacrylate functionality.

Even further, the endblocking agent may be described to be of the general formula $XYR^1_bSiZ_{3-b}$ wherein X is a monovalent radical of the general formula AE- where E is —O— or —NH— and A is an acryl group or a methacryl group as set forth above, Y is a divalent alkylene radical having from 1 to 6 carbon atoms, R' is a methyl or a phenyl radical, Z is a monovalent hydrolyzable organic radical or a halogen, and b is 0, 1, or 2. Preferably, the monovalent hydrolyzable organic radical is of the general formula R"O— where R" is an alkylene radical. Most preferably, this particular endblocking agent is selected from the group of 3-methacryloxypropyldimethylchlorosilane, 3-methacryloxypropyldichlorosilane, 3-methacryloxypropyltrichlorosilane, 3-methacryloxypropyldimethylmethoxysilane, 3-methacryloxypropylmethyldimethoxysilane, 3-meth-acryloxypropyltrimethoxysilane, 3-methacryloxypropyldimethylethoxysilane, 3-methacryloxypropylmethyldiethoxysilane, 3-methacryloxypropyltriethoxysilane, (methacryloxymethyl)dimethylmethoxysilane, (methacryloxymethyl)methyldimethoxysilane, (methacryloxymethyl)trimethoxysilane, (methacryloxymethyl)dimethylethoxysilane, (methacryloxymethyl)methyldiethoxysilane, methacryloxymethyltriethoxysilane, methacryloxy-propyltriisopropoxysilane, 3-methacryloxypropyldimethylsilazane, 3-acryloxy-propyldimethylchlorosilane, 3-acryloxypropyldichlorosilane, 3-acryloxypropyl-trichlorosilane, 3-acryloxypropyldimethylmethoxy-silane, 3-acryloxy-propylmethyldimethoxysilane, 3-acryloxypropyltrimethoxysilane, 3-acryloxypropyl-dimethylsilazane, and combinations thereof.

As alluded to above, the second silicon-containing capping agent can be used in conjunction with the silicon-containing capping, or endblocking, agent in embodiments of the present invention. This second silicon-containing capping agent is distinguishable from the silicon-containing capping agent in that the second silicon-containing capping agent is free of acrylate and methacrylate functionality. If included, the second silicon-containing capping agent, an organosilicon endblocking agent, is along with the silicon-containing capping agent and the pressure sensitive adhesive a reaction product that forms the composition. The second silicon-containing capping agent is capable of generating an endblocking triorganosilyl unit.

Forming the Silicone Acrylic Hybrid Composition

The silicone acrylic hybrid compositions used in the embodiments of the present invention are visco-elastic compositions. Preferably, these take the form of pressure sensitive adhesives (also commonly referred to as PSAs); however, the visco-elastic compositions can also be non-adhesive materials as in film formers. The silicone acrylic hybrid compositions comprise the reaction product of the silicon-containing pressure sensitive adhesive composition, the ethylenically unsaturated monomer, and the initiator in the presence of a solvent. That is, the silicone acrylic hybrid compositions are the product of the chemical reaction between these reactants (the silicon-containing pressure sensitive adhesive composition, the ethylenically unsaturated monomer, and the initiator in the presence of a solvent). The term "pressure sensitive adhesive" and the acronym "PSA" are used interchangeably throughout the subject description. As just one example, the silicon-containing pressure sensitive adhesive composition may also be referred to as the silicon-containing PSA composition. The silicone acrylic hybrid compositions used in the present invention may also be referred to as silicone acrylate hybrid compositions; the term "silicone acrylic hybrid composition" is used interchangeably with the term "silicone acrylate hybrid composition" in the subject description. As used herein, the terms silicone acrylate and silicone acrylic are intended to denote more than a simple blend of a silicone-based sub-species and an acrylate-based sub-species. Instead, these terms denote a polymerized hybrid species that includes silicone-based sub-species and acrylate-based sub-species that have been polymerized together.

The Ethylenically Unsaturated Monomer

As originally described above, the ethylenically unsaturated monomer is a reactant that, along with the silicon-containing pressure sensitive adhesive composition and the initiator, reacts to form the silicone acrylic hybrid composition used in embodiments of the present invention. More specifically, in the method of making the silicone acrylic hybrid composition used in embodiments of the present invention, once the silicon-containing pressure sensitive adhesive composition described above is provided, the ethylenically unsaturated monomer and the silicon-containing pressure sensitive adhesive composition are polymerized in a first solvent in the presence of an initiator to form a silicone acrylic hybrid composition. The ethylenically unsaturated monomer is preferably present in the silicone acrylic hybrid composition in an amount of from about 5 to about 95, more preferably from about 25 to about 75, and still more preferably from about 40 to about 60 parts by weight based on 100 parts by weight of the silicone acrylic hybrid composition. Although the present invention is described primarily as including one ethylenically unsaturated monomer, it is to be understood that more than one ethylenically unsaturated monomer, i.e., a combination of ethylenically unsaturated monomers, may be polymerized, more specifically co-polymerized, along with the silicon-containing pressure sensitive adhesive composition and the initiator. Generally, the acrylic portion of the silicone acrylic hybrid composition formed via the reaction of the ethylenically unsaturated monomer and the silicon-containing pressure sensitive adhesive composition is typically formed similar to acrylate-based PSAs with a combination of monomers that can be broadly described as a main monomer and a modifying monomer as is described extensively in Chapter 19 of the Handbook of Pressure Sensitive Adhesive Technology, Third Edition, Donatas Satas, Satas & Associates, 1999, Warwick, R.I.

The ethylenically unsaturated monomer can be any monomer having at least one carbon-carbon double bond. It is preferred that the ethylenically unsaturated monomer used in the processes of the present invention is a compound selected from the group of aliphatic acrylates, aliphatic methacrylates, cycloaliphatic acrylates, cycloaliphatic methacrylates, and combinations thereof. It is to be understood that each of the compounds, the aliphatic acrylates, the aliphatic methacrylates, the cycloaliphatic acrylates, and the cycloaliphatic methacrylates, include an alkyl radical. The alkyl radicals of these compounds can include up to 20 carbon atoms.

The aliphatic acrylates that may be selected as one of the ethylenically unsaturated monomers are selected from the group consisting of methyl acrylate, ethyl acrylate, propyl acrylate, n-butyl acrylate, iso-butyl acrylate, tert-butyl acrylate, hexyl acrylate, 2-ethylhexyl acrylate, iso-octyl acrylate, iso-nonyl acrylate, iso-pentyl acrylate, tridecyl acrylate, stearyl acrylate, lauryl acrylate, and mixtures thereof. The aliphatic methacrylates that may be selected as one of the ethylenically unsaturated monomers are selected from the group consisting of methyl methacrylate, ethyl methacrylate, propyl methacrylate, n-butyl methacrylate, iso-butyl meth-acrylate, tert-butyl methacrylate, hexyl methacrylate, 2-eth-ylhexyl methacrylate, iso-octyl methacrylate, iso-nonyl methacrylate, iso-pentyl methacrylate, tridecyl methacrylate, stearyl methacrylate, lauryl methacrylate, and mixtures thereof. The cycloaliphatic acrylate that may be selected as one of the ethylenically unsaturated monomers is cyclohexyl acrylate, and the cycloaliphatic methacrylate that may be selected as one of the ethylenically unsaturated monomers is cyclohexyl methacrylate.

Certain other monomers, described herein as polar monomers, may be used as the ethylenically unsaturated monomer and may include supplemental functionality such as hydroxyl functionality. A polar monomer as used herein is an acrylic or methacrylic monomer having at least one polar group such as hydroxyl, alkoxy, amino, and alkenyl heterocycles. Examples of these polar monomers that are useful in the present invention include, but are not limited to, hydrophilic ethylenically unsaturated monomers of an amphoteric, anionic, cationic or anionic nature which are polymerizable by radical polymerization. More specific examples of these polar monomers include, but are not limited to, acrylic acid, methacrylic acid, itaconic acid, vinyl acetate, vinyl acetic acid, hydroxy ethyl acrylate, hydroxy ethyl methacrylate, hydroxy propyl acrylate, hydroxy propyl methacrylate, methoxyethyl acrylate, meth-oxyethyl methacrylate, amino-ethyl acrylate, aminoethyl methacrylate, 2-N,N,N-trimethylammonium ethyl acrylate, 2-N,N,N-trimethylammonium ethyl methacrylate, acrylonitrile, methacrylonitrile, N,N-dimethylacrylamide, N-t-butylacrylamide, acrylamide, N-vinyl pyrrolidone, 2-acrylamido-2-methyl propane sulphonic acid, or salts thereof and the like.

The ethylenically unsaturated monomer and the silicon-containing pressure sensitive adhesive composition are polymerized in a first solvent in the presence of the initiator. It is generally preferred that the polymerization of the ethylenically unsaturated monomer and the silicon-containing pressure sensitive adhesive composition in the first solvent in the presence of the initiator is conducted at a temperature of from 50° C. to 100° C., more preferably of from 65° C. to 90° C. It is to be understood that the method of the present invention can be employed in a batch process, semi-continuous process, or continuous process. The method of the present invention is also 'flexible' in that the method accounts for rate controlled addition of the ethylenically unsaturated monomer or monomers which also contributes to the ability to control the silicone to acrylic ratio as described below.

The First Solvent

The first solvent used to form the silicone acrylic hybrid composition decreases the viscosity of the reaction mixture which allows for adequate mixing and heat transfer. The first solvent may be any suitable material which is inert to the reaction ingredients and does not interfere with the reaction itself. The first solvent may be, but is not limited to, aliphatic hydrocarbons such as hexane and heptane; ketones such as acetone, methyl ethyl ketone and methyl isobutyl ketone; esters such as ethyl acetate, n-butyl acetate and i-butyl acetate; low viscosity silicone oils with linear, cyclic or branched structures which have a boiling point below 250° C. and a viscosity below 100 centistokes such as octamethylcyclotetrasiloxane, decamethylcyclopentasiloxane and hexamethyldisiloxane; and mixtures of two or more of the above mentioned solvents. The amount of first solvent is preferably present in an amount of from about 30 to about 95, more preferably from about 40 to about 85, and still more preferably from about 50 to about 75 parts by weight based on the total amount of the reactants and solvent. Preferably, the first solvent will have a boiling point less than that of the second solvent to facilitate the in-process solvent exchange as described below.

The Initiator

It is to be understood that there are many different initiation mechanisms contemplated for use in the present invention to initiate the polymerization of the silicon-containing pressure sensitive adhesive composition and the ethylenically unsaturated monomer to form the silicone acrylic hybrid composition. However, the preferred initiator is that known throughout the art as a free radical initiator and is detailed in Chapter 3 of Principles of Polymerization, Fourth Edition, George Odian, Wiley-Interscience, 2004, New Jersey. Generally, free radical initiators include peroxides, azo compounds, redoxinitiators, and photo-initiators. The most preferred free radical initiators for application in the present invention are selected from the group of peroxides, azo compounds, and combinations thereof. The initiator is preferably present in the silicone acrylic hybrid composition in an amount of from 0.005 to 3, more preferably from 0.01 to 2, parts by weight based on 100 parts by weight of the silicone acrylic hybrid composition.

During the polymerization of the ethylenically unsaturated monomer and the silicon-containing pressure sensitive adhesive composition, the silicone to acrylic ratio can be controlled and optimized as desired. The silicone to acrylic ratio can be controlled by a wide variety of mechanisms in and during the method. An illustrative example of one such mechanism is the rate controlled addition of the ethylenically unsaturated monomer or monomers to the silicon-containing pressure sensitive adhesive composition. In certain applications, it may be desirable to have the silicone-based sub-species, or the overall silicone content, to exceed the acrylate-based sub-species, or the overall acrylic content. In other applications, it may be desirable for the opposite to be true. Independent of the end application, it is generally preferred, as already described above, that the silicon-containing pressure sensitive adhesive composition is preferably present in the silicone acrylic hybrid composition in an amount of from about 5 to about 95, more preferably from about 25 to about 75, and still more preferably from about 40 to about 60 parts by weight based on 100 parts by weight of the silicone acrylic hybrid composition.

Optional Step of Blending the Silicone Acrylic Hybrid Composition with a Non-Hybrid Pressure Sensitive Adhesive Composition Optionally, after step (ii), the silicone acrylic hybrid composition from step (ii) is blended with a non-hybrid pressure sensitive adhesive composition. This blending step facilitates in selectively controlling the phase arrangement of the multi-phase silicone acrylic hybrid visco-elastic composition described below. The non-hybrid pressure sensitive adhesive compositions include, but are not limited to, other silicone pressure sensitive adhesive compositions, acrylic pressure sensitive adhesive compositions, polyurethane pressure sensitive adhesive compositions, natural rubber pressure sensitive adhesive compositions, synthetic rubber pressure sensitive adhesive compositions, and blends, e.g. physical blends, thereof. One such blend is a blend of acrylic and rubber pressure sensitive adhesive compositions.

Alternatively, the methods described herein optionally and preferably further include the step of blending the multi-phase silicone acrylic hybrid visco-elastic composition described below with a non-hybrid pressure sensitive adhesive composition as described in detail below.

Removal of the First Solvent in Embodiment One, Step (iii) of the Invention

In Embodiment One of the Invention, upon formation of the silicone acrylic hybrid composition, the first solvent is removed in step (iii) to less than 5 parts, preferably less than 1 part, by weight based on 100 parts by weight of the silicone acrylate hybrid solids. The first solvent may be removed by suitable techniques for solvent removal including, but not limited to, heat, vacuum, or combinations thereof.

Addition of Second Solvent in Embodiment One, Step (iv) of the Invention to Form the Multi-Phase Silicone Acrylic Hybrid Visco-Elastic Composition In Embodiment One of the Invention, following removal of the first solvent in step (iii), a second solvent is added in step (iv) to form the multi-phase silicone acrylic hybrid visco-elastic composition. Further details about the multi-phase silicone acrylic hybrid visco-elastic composition are detailed below. The addition of the second solvent is typically performed under agitation to facilitate mixing of the reaction ingredients. The second solvent may be, but is not limited to, a volatile silicone (hexamethyldisiloxane, octamethyltrisiloxane, cyclomethicone and the like), an aliphatic solvent (hexane, cyclohexane, heptane, isododecane and the like), an aromatic solvent (toluene, xylene and the like), a ketone (acetone, methyl ethyl ketone and the like), an ester (ethyl acetate, butyl acetate and the like), a halogenated solvent (dichloromethane, Freon, and the like), a mineral spirit (naptha, Stoddard solvent and the like), and combinations thereof. The amount of second solvent is preferably present in an amount of from about 5 to about 95, more preferably from about 20 to about 80, and still more preferably from about 40 to about 60 parts by weight based on the total amount of the reactants. The amount of second solvent added and the resulting mixture viscosity is matched to the desired end use (for example, coating or spraying).

Addition of Processing Solvent in Embodiment Two, Step (iii) of the Invention

In Embodiment Two of the Invention, upon formation of the silicone acrylic hybrid composition in step (ii) and optionally partial removal of the first solvent, a processing solvent is added to the silicone acrylic hybrid composition in step (iii). Preferably, the processing solvent has a higher boiling point than the first solvent. The addition of the processing solvent is typically performed under agitation to facilitate mixing of the reaction ingredients. The processing solvent may be, but is not limited to, a volatile silicone (hexamethyldisiloxane, octamethyltrisiloxane, cyclomethicone and the like), an aliphatic solvent (hexane, cyclohexane, heptane, isododecane and the like), an aromatic solvent (toluene, xylene and the like), a ketone (acetone, methyl ethyl ketone and the like), an ester (ethyl acetate, butyl acetate and the like), a halogenated solvent (dichloromethane, Freon, and the like), a mineral spirit (naptha, Stoddard solvent and the like), and combinations thereof, provided that the processing solvent which is selected for use in Embodiment Two has a higher boiling point than the first solvent.

The use of a processing solvent with a higher boiling point than the first solvent is important to facilitate removal of the first, lower boiling point solvent when heat is applied in the next step (step (iv)) detailed below. The difference between the boiling points of the first solvent and processing solvent causes selective removal of the first solvent to a desired amount upon applying heat as detailed below. The amount of processing solvent is preferably present in an amount of from about 5 to about 95, more preferably from about 20 to about 80, and still more preferably from about 40 to about 60 parts by weight based on the total amount of the material.

Application of Heat in Embodiment Two, Step (iv) of the Invention to Selectively Remove the First Solvent In Embodiment Two of the Invention, upon addition of the processing solvent, heat is applied in step (iv) at a temperature of from 70° C. to 200° C. such that the first solvent is selectively removed. The temperature may more preferably be from 70° C. to 150° C. such that the majority of the first solvent is selectively removed to less than 30 parts, preferably less than 20 parts, by weight based on 100 parts by weight total solvent. As detailed above, the application of heat causes the first, lower boiling point solvent to be preferentially removed.

Removal of Processing Solvent in Embodiment Two, Step (v) of the Invention

In Embodiment Two of the Invention, after step (iv), the processing solvent is removed in step (v) to less than 5 parts, preferably less than 1 part, by weight based on 100 parts by weight of the silicone acrylate hybrid solids. The processing solvent may be removed by suitable techniques for solvent removal including, but not limited to, heat, vacuum, or combinations thereof.

Addition of Second Solvent in Embodiment Two, Step (vi) of the Invention to Form the Multi-Phase Silicone Acrylic Hybrid Visco-Elastic Composition In Embodiment Two of the Invention, following removal of the processing solvent in step (v), a second solvent is added in step (vi) to form the multi-phase silicone acrylic hybrid visco-elastic composition. Further details about the multi-phase silicone acrylic hybrid visco-elastic composition are detailed below. The addition of the second solvent is typically performed under agitation to facilitate mixing of the reaction ingredients. The second solvent may be, but is not limited to, a volatile silicone (hexamethyldisiloxane, octamethyltrisiloxane, cyclomethicone and the like), an aliphatic solvent (hexane, cyclohexane, heptane, isododecane and the like), an aromatic solvent (toluene, xylene and the like), a ketone (acetone, methyl ethyl ketone and the like), an ester (ethyl acetate, butyl acetate and the like), a halogenated solvent (dichloromethane, Freon, and the like), a mineral spirit (naptha, Stoddard solvent and the like), and combinations thereof. The amount of second solvent is preferably present in an amount of from about 5 to about 95, more preferably from about 20 to about 80, and still more preferably from about 40 to about 60 parts by weight based on the total amount of the reactants. The amount of second solvent added and the resulting mixture viscosity is matched to the desired end use (for example, coating or spraying).

The Multi-Phase Silicone Acrylic Hybrid Visco-Elastic Composition

The processes of the present invention facilitate the phase or domain arrangement of the resulting multi-phase silicone acrylic hybrid visco-elastic composition to be selectively controlled. Depending on the selection of the second solvent, the resulting multi-phase silicone acrylic hybrid visco-elastic compositions contain (1) a continuous, silicone external phase and a discontinuous, acrylic internal phase or (2) a continuous, acrylic external phase and a discontinuous, silicone internal phase as selectively controlled by selection of the second solvent. Where the continuous, silicone external phase and the discontinuous, acrylic internal phase is present, acrylic domains surround silicone subdomains. Where the continuous, acrylic external phase and the discontinuous, silicone internal phase is present, silicone domains surround acrylic subdomains.

The phase or domain arrangement of the multi-phase silicone acrylic hybrid visco-elastic composition is selectively controlled or manipulated by selection of the second solvent. Stated another way, the external phase of the multi-phase silicone acrylic hybrid visco-elastic composition varies with the selection of the second solvent in which the multi-phase silicone acrylic hybrid visco-elastic composition is made and re-dispersed. The physiochemical properties of the multi-phase silicone acrylic hybrid visco-elastic composition are selectively controllable by the phase or domain arrangement that is achieved. Likewise, by selectively controlling the phase arrangement of the multi-phase silicone acrylic hybrid visco-elastic composition, the drug release properties of the multi-phase silicone acrylic hybrid visco-elastic composition can be selectively controlled or adjusted as desired. Acrylic domains dispersed in a continuous, silicone external phase can be achieved as desired. In contrast, silicone domains, for example, dispersed in a continuous, acrylic external phase can also be achieved as desired. For example, where the second solvent is heptane, the multi-phase silicone acrylic hybrid visco-elastic composition contains a silicone external phase. This might be desired in settings where, for example, when higher shear strength is desired. Where, for instance, the second solvent is ethyl acetate, the multi-phase silicone acrylic hybrid visco-elastic composition contains an acrylate external phase. This might be desired in settings where, for example, when higher tack is desired. The physiochemical properties of the multi-phase silicone acrylic hybrid visco-elastic composition which can be selectively controlled or adjusted as desired using the processes described herein include, but are not limited to, tack, adhesion, peel release from liner, drug solubility, active release, active release profile, rheology (creep behavior including cold flow), and viscosity. The domain arrangement is selected to match the requirements for specific material performance as related to patch construction, active delivery, processing conditions and the like.

Preferably, the ratio of silicone to acrylate in the multi-phase silicone acrylic hybrid visco-elastic composition formed by the methods described herein is from 5 parts silicone to 95 parts acrylate or 95 parts silicone to 5 parts acrylate to facilitate selectively controlling the phase arrangement of the multi-phase silicone acrylic hybrid visco-elastic composition. More preferably, the ratio of silicone to acrylate is from 20 parts silicone to 80 parts acrylate or 80 parts silicone to 20 parts acrylate to facilitate selectively controlling the phase arrangement of the multi-phase silicone acrylic hybrid visco-elastic composition. Still more preferably, the ratio of silicone to acrylate is from 40 parts silicone to 60 parts acrylate or 60 parts silicone to 40 parts acrylate to facilitate selectively controlling the phase arrangement of the multi-phase silicone acrylic hybrid visco-elastic composition.

The multi-phase silicone acrylic hybrid visco-elastic composition may be delivered in liquid in form or as a solid to be used as a hot melt.

Optional Step of Blending the Multi-Phase Silicone Acrylic Hybrid Visco-Elastic Composition with a Non-Hybrid Pressure Sensitive Adhesive Composition Optionally, once the multi-phase silicone acrylic hybrid visco-elastic composition is formed (that is, after step (iv) in Embodiment One of the Invention or after step (vi) in Embodiment Two of the Invention), the multi-phase silicone acrylic hybrid visco-elastic composition is blended with a non-hybrid pressure sensitive adhesive composition. This blending step facilitates in selectively controlling the phase arrangement of the multi-phase silicone acrylic hybrid visco-elastic composition. The non-hybrid pressure sensitive adhesive compositions include, but are not limited to, other silicone pressure sensitive adhesive compositions, acrylic pressure sensitive adhesive compositions, polyurethane pressure sensitive adhesive compositions, natural rubber pressure sensitive adhesive compositions, synthetic rubber pressure sensitive adhesive compositions, and blends, e.g. physical blends, thereof.

Uses of the Multi-Phase Silicone Acrylic Hybrid Visco-Elastic Composition

The multi-phase silicone acrylic hybrid visco-elastic composition can be applied or coated onto a substrate using any suitable technique including, but not limited to, solvent-based coating techniques known in the art including knife-over-roll, Gravure, or the like. The multi-phase silicone acrylic hybrid visco-elastic composition can be dried to form a visco-elastic polymer film on the substrate. The drying can be performed by any suitable technique including, but not limited to, use of a conventional oven and other heating techniques known in the art. Alternatively, the composition can be sprayed onto the desired substrate and allowed to dry. The visco-elastic polymer film layer that results on the substrate may be tacky or non-tacky depending on the hybrid composition and the domain arrangement. The visco-elastic polymer film may be a pressure sensitive adhesive or a non-tacky film former. The physiochemical properties of the multi-phase silicone acrylic hybrid visco-elastic composition detailed above are imparted to the film. The drug release properties of the multi-phase silicone acrylic hybrid visco-elastic composition detailed above are also imparted to the film.

In many of the applications described in the present invention, including tapes, labels and transdermal drug delivery systems, it is often necessary to use a backing layer and a release layer. The backing layer can be any of the typical substrates used for tapes such as those selected from polymeric films (e.g. polyethylene, polyester, polyimide, polyolefins, polypropylene, polyurethane, PTFE, etc.), metal foils, glass cloth, PTFE-coated glass cloth, paper (e.g. crepe, super-calendared craft, etc.), cloth, nonwoven materials, foams (e.g. polyurethane, acrylate, silicone, neoprene, etc.) and rubbers (e.g. silicone, butyl, etc.). Release liners are generally supplied on a backing such as paper or film and are applied to the multi-phase silicone acrylic hybrid visco-elastic composition after the drying and/or curing steps are complete. Three general types of release coatings the are suitable for use with both silicone-based PSAs and acrylate-based PSAs, and also with the multi-phase silicone acrylic hybrid visco-elastic compositions of the present invention are known in the art and are commercially available: silicone-based release liners (e.g. Dow Corning® Syl-Off™ 7680, Dow Corning Corp., Midland Mich.), perfluoropolyether-based release liners (e.g. 3M SCOTCH-PAK® 1022 Release Liner) and fluorosilicone-based release liners (e.g. Dow Corning® Syl-Off™ Q2-7785). The release liner for a particular application will be dependent upon the domain arrangement of the final multi-phase silicone acrylic hybrid visco-elastic composition after removal of the second solvent to form the visco-elastic polymer film. If the silicone phase is external a fluorinated release liner is preferred while a silicone-based release liner may be preferred if the acrylate phase is external.

These adhesives (the multi-phase silicone acrylic hybrid visco-elastic compositions) are also particularly suited for other electronic monitoring and medical device attachment applications that require adhering medical devices to the skin or body. Other end uses that this material may be especially suited for include film formers for the protection and/or delivery of active agents to skin, nail, hair or other biological tissues. Film formers are those visco-elastic materials that when applied to biological substrates such as skin, teeth, mucosa or plants form a thin, flexible continuous, semi-continuous or discontinuous layer of the viscoelastic material that adheres to the biological substrate and performs a desired function. Typical functions for films include delivery of active agents to the surface of the biological surface, to an intermediate layer of the biological surface or completely through the biological surface. Alternatively, the films may be used to protect the skin from external stimuli, including pollution, moisture or chemicals. Alternatively, the materials of this invention can be used as components of semisolid drug delivery compositions where they can impart thickening, substantivity, and other benefits to the formulations.

One particularly important application for the multi-phase silicone acrylic hybrid visco-elastic compositions of the present invention is in a transdermal drug delivery system. The transdermal drug delivery system includes an active agent and the multi-phase silicone acrylic hybrid visco-elastic compositions of the present invention functioning as a pressure sensitive adhesive. The active agent and its relationship to the multi-phase silicone acrylic hybrid visco-elastic composition in the context of the transdermal drug delivery system are described in detail below. As those skilled in the art appreciate, the transdermal drug delivery system is structural and can be in many forms including, but not limited to, patches, films, multi-layer dressings, reservoir systems, and combinations thereof. The active agent is in the transdermal drug delivery system for controlled transdermal delivery to a substrate. It is also possible, but not required, for the transdermal drug delivery system to include a backing layer for supporting the multi-phase silicone acrylic hybrid visco-elastic composition, and/or a release liner for protecting the multi-phase silicone acrylic hybrid visco-elastic composition and/or the active agent prior to the controlled transdermal delivery of the active agent to the substrate. One preferred application of the transdermal drug delivery system of the present invention is to treat a user, or patient, with the active agent. As a result, the substrate is typically the skin of the user and, in this preferred application, the user applies and wears the transdermal drug delivery system on their skin. The active agent can be any component suitable for trans-dermal delivery to a substrate.

Where the multi-phase silicone acrylic hybrid visco-elastic compositions of the present invention are used in transdermal drug delivery systems, numerous advantages are provided. For example, the phase arrangement can be selectively controlled to achieve desired wear properties. The multi-phase silicone acrylic hybrid visco-elastic compositions can affect the drug solubility and thereby prevent drug crystallization within a transdermal device or patch. The multi-phase silicone acrylic hybrid visco-elastic compositions can also affect the drug solubility and the location where the drug compartmentalizes within the dried film of the transdermal device. The multi-phase silicone acrylic hybrid visco-elastic compositions described herein are useful in transdermal drug delivery applications to aid in controlling the elution rates of drug(s) from the transdermal device or patch.

As those skilled in the art appreciate, the active agents can be present in the transdermal drug delivery system in different forms, depending on which form yields optimum delivery characteristic, such as the release rate and the total amount released as described below. For example, in the case of drugs, the drug can be in its free base or acid form, or in the form of salts, esters, or any other pharmacologically acceptable derivatives, or even as components of molecular complexes.

The amount of the active agent incorporated into the transdermal drug delivery system varies depending on many factors including, but not limited to, the particular active agent, the desired therapeutic effect, and the time span for which the system is to provide therapy. For most active agents, the passage of the active agent through the skin is the rate-limiting step in transdermal delivery. Thus, the amount of the active agent and the rate of release are typically selected so as to provide transdermal delivery characterized by a zero order time dependency for a prolonged period of time. The minimum amount of active agent in the transdermal drug delivery system is selected based on the amount of active agent which passes through the skin, or other substrate, in the time span for which the system is to provide therapy. Preferably, the amount of active agent in the transdermal drug delivery system varies from about 0.1% up to about 60% by weight of the system, more preferably from about 0.3% up to about 50% by weight of the system, and for the lower drug doses permitted by this invention, most preferably from about 1.0% up to about 30% by weight of the system. The weight of the transdermal drug delivery system is, at a minimum, the combined weight of the active agent and the multi-phase silicone acrylic hybrid visco-elastic composition. Examples of active agents for use in the transdermal drug delivery systems described herein can include, but are not limited to, hypertensives, like ACE inhibitors and beta blockers, steroids, including corticosteroids and other natural and synthetic steroids, hormones, including androgens and estrogens and progestragens, anti-fungals including imidazoles and thioazole anti-fungals, antihelmintics for example benzimidazoles, pain relievers such as opiates and steroids, stimulants such as methylphenidate, and other topically and transdermally-administered active agents.

Of course, the transdermal drug delivery system can also contain other agents known to accelerate the delivery of the active agent through the skin or other substrate. These other agents are also referred to in the art as skin-penetration or permeation enhancers, accelerants, adjuvants, and sorption promoters, and are collectively referred herein simply as "enhancers". These enhancers includes those with diverse mechanisms of action including those which have the function of improving the solubility and diffusibility of the active agent within the multi-phase silicone acrylic hybrid visco-elastic composition and those which improve percutaneous absorption, for example, by changing the ability of the stratum corneum to retain moisture, softening the skin, improving the skin's permeability, acting as penetration assistants or hair-follicle openers or changing the state of the skin including the boundary layer. Some of these enhancers have more than one mechanism of action, but in essence they serve to enhance the delivery of the active agent to the substrate.

Other applications for the multi-phase silicone acrylic hybrid visco-elastic composition include, but are not limited to, tapes, labels, notes, bandages, transdermal drug delivery systems (e.g. patches), medical device attachments, lipstick, nail varnish, hair spray, hair fixatives, and other cosmetic products, transfer adhesives, laminating adhesives, surface priming, and vibration damping. Use of the multi-phase silicone acrylic hybrid visco-elastic compositions allows one to control the physiochemical properties of these end products by selectively controlling the domain arrangement to impart desired physical properties such as minimal cold flow, suitable peel release, adhesion, thermo-response, active release and wear properties to the end products

EXAMPLES

The following examples illustrating specifics associated with the making of the multi-phase silicone acrylic hybrid visco-elastic compositions of the present invention, as presented herein, are intended to illustrate and not limit the invention. All parts and percentages in the examples are on a weight basis and all measurements were indicated at about 23° C., unless indicated to the contrary.

Example 1: Preparation of Silicon-Containing Pressure Sensitive Adhesive Composition in Ethyl Acetate PSA 1 is a silicon-containing pressure sensitive adhesive composition and was prepared by blending the hydroxy end-blocked polydimethylsiloxane, trimethylsiloxy-hydroxy end-blocked silicate resin solution, and xylene together in the reaction vessel at about 72% non-volatile content (% NVC). The mixture was then heated to approximately 115° C. Anhydrous ammonia gas was passed through the solution to promote the "bodying" condensation reaction. After completion of the bodying reaction, volatile components (such as xylene, ammonia and low molecular weight silicone materials) were removed from the reaction mixture with heat and vacuum. The adhesive solids were re-solvated in ethyl acetate to achieve 60% solids content. After re-solvating in ethyl acetate, the silicon-containing pressure sensitive adhesive composition was functionalized by adding the appropriate amount of 3-methacryloxypropyldimethylchlorosilane, calculated based on adhesive solids, to the silicon-containing pressure sensitive adhesive composition in a kettle and mixed for a predetermined amount of time to complete the reaction. Sodium bicarbonate was added to neutralize the hydrochloric acid generated and subsequently removed via filtration. The methacrylate capping reaction was carried out under continuous agitation.

Example 2: Preparation of Silicon-Containing Pressure Sensitive Adhesive Composition in Heptane PSA 2 is a silicon-containing pressure sensitive adhesive composition and was prepared by blending the hydroxy end-blocked polydimethylsiloxane, trimethylsiloxy-hydroxy end-blocked silicate resin solution, and xylene together in the reaction vessel at about 72% non-volatile content (% NVC). The mixture was then heated to approximately 115° C. Anhydrous ammonia gas was passed through the solution to promote the "bodying" condensation reaction. After completion of the bodying reaction, volatile components (such as xylene, ammonia and low molecular weight silicone materials) were removed from the reaction mixture with heat and vacuum. The adhesive solids were re-solvated in heptane to achieve 60% solids content. After re-solvating in heptane, the silicon-containing pressure sensitive adhesive composition was functionalized by adding the appropriate amount of 3-methacryloxypropyldimethylchlorosilane, calculated based on adhesive solids, to the silicon-containing pressure sensitive adhesive composition in a kettle and mixed for a predetermined amount of time to complete the reaction. Sodium bicarbonate was added to neutralize the hydrochloric acid generated and subsequently removed via filtration. The methacrylate capping reaction was carried out under continuous agitation.

Example 3: Preparation of Low Tack Silicone Acrylic Hybrid Composition in Ethyl Acetate PSA 3 is a low tack silicone acrylic hybrid composition which was prepared as follows: In a suitable reactor, materials were added in the following ratio: 25% 2-ethylhexyl acrylate (2-EHA), 25% methyl acrylate (MA), 50% capped silicon-containing PSA composition (PSA 1 of Example 1) based on solids, ethyl acetate and Vazo 67 initiator (0.145 parts per hundred monomer) were added to form a pre-reaction mixture (58.5% reactants). The materials in this pre-reaction mixture were allowed to stir approximately 30 minutes until thoroughly homogeneous. After mixing, an aliquot (of approximately 25% of the total amount) of the pre-reaction mixture and ethyl acetate were added to a glass lined reactor to achieve a concentration 22.8% pre-reaction mixture, 77.2% solvent. The reaction temperature was set at 78° C. As soon as the reaction temperature was achieved, the mixture was allowed to react for 60 minutes prior to feeding the remaining pre-reaction mixture to the reactor over a 3 hr period using a metering pump. The mixture in the reactor was then reacted at 78° C. for an additional 20 hr. To this, hexamethyldisilazane and trifluoroacetic acid were added to endblock the remaining hydroxy functionality on the adhesive and mixed for a predetermined amount of time. At the end of the capping reaction, 2-propanol and deionized water were added and subsequently stripped to remove the residual trifluoroacetic acid and to form the silicone acrylic hybrid composition.

Example 4: Preparation of Low Tack Silicone Acrylic Hybrid Composition in Heptane PSA 4 was prepared in a similar fashion to Example 3 using PSA 2 from Example 2 and heptane instead of ethyl acetate as the solvent.

Example 5: Preparation of High Tack Silicone Acrylic Hybrid Composition in Ethyl Acetate PSA 5 is the analogous high tack silicone acrylic hybrid compositions and was prepared as follows: In a suitable reactor, materials were added in the following ratio: 30% 2-EHA, 20% MA, 50% capped silicon-containing PSA composition (PSA 1 from Example 1) solids, ethyl acetate and Vazo 67 initiator (0.145 parts per hundred monomer), were added to form a pre-reaction mixture (58.5% reactants). The materials in this pre-reaction mixture were allowed to stir approximately 30 minutes until thoroughly homogeneous. After mixing, an aliquot (of approximately 25% of the total amount) of the pre-reaction mixture and ethyl acetate were added to a glass-lined reactor to achieve a concentration 22.8% pre-reaction mixture, 77.2% solvent. The reaction temperature was set at 78° C. As soon as the reaction temperature was achieved, the mixture was allowed to react for 60 minutes prior to feeding the remaining pre-reaction mixture to the reactor over a 3 hr period using a metering pump. The mixture in the reactor was then reacted at 78° C. for an additional 20 hr. To this, hexamethyldisilazane and trifluoroacetic acid were added to end-block the remaining hydroxy functionality on the adhesive and mixed for a predetermined amount of time. At the end of the capping reaction, 2-propanol and deionized water were added and subsequently stripped to remove the residual trifluoroacetic acid and to form the silicone acrylic hybrid composition.

Example 6: Preparation of High Tack Silicone Acrylic Hybrid Composition in Heptane PSA 6 was prepared in a similar fashion to Example 5 using PSA 2 from Example 2 and heptane instead of ethyl acetate as the solvent.

Example 7: Preparation of the Multi-Phase Silicone Acrylic Hybrid Visco-Elastic Compositions PSA 3-6 were extruded to remove the first solvent (ethyl acetate or heptane) and re-dispersed in a second solvent (ethyl acetate or heptane) at 50% solids based on weight to create the multi-phase silicone acrylic hybrid visco-elastic compositions.

TABLE 1

Materials Used in Preparing the Multi-Phase Silicone Acrylic Hybrid Visco-Elastic Compositions

| Sample No. | Silicone Acrylic Hybrid Composition | Solvent 1 | Solvent 2 |
|---|---|---|---|
| PSA 7 | Example 3 | Ethyl acetate | Heptane |
| PSA 8 | Example 3 | Ethyl acetate | Ethyl acetate |
| PSA 9 | Example 4 | Heptane | Heptane |
| PSA 10 | Example 4 | Heptane | Ethyl acetate |
| PSA 11 | Example 5 | Ethyl acetate | Heptane |
| PSA 12 | Example 5 | Ethyl acetate | Ethyl acetate |
| PSA 13 | Example 6 | Heptane | Heptane |
| PSA 14 | Example 6 | Heptane | Ethyl acetate |

The physical properties of the hybrid pressure sensitive adhesives can be controlled by adjusting the ratio of the acrylic monomers used to create the adhesives. The hybrid produced using a ratio of 50% 2-EHA and 50% MA as the acrylate component of the silicone-acrylic hybrid PSA had a lower relative tack than a PSA produced using a ratio of 60% 2-EHA and 40% MA as the acrylate component. These adhesives may be referred to as "low tack" and "high tack" respectively. The polymerization solvent was ethyl acetate or heptane. The solvent was removed by heating and aliquots of the adhesive solids were re-dissolved in either ethyl acetate or heptane.

It was discovered that the appearance of adhesives (PSA 3-6) re-dissolved in ethyl acetate differed from those re-dissolved in heptane. When the material was re-dissolved in ethyl acetate to achieve 50% solids, the final product was opaque light yellow in appearance. When the resulting material was dispersed in heptane to achieve 50% solids, the final product was white in color. However, the appearance of materials re-dispersed in each respective second solvent was the same regardless of the first solvent or the ratio of 2-EHA:MA. The results are shown in Table 2.

In addition to the color differences observed depending on the second solvent selected, it was noted that the materials dispersed in ethyl acetate exhibited different pouring and flowing behavior than those in heptane. Following the visual examination of the solvated adhesive, the volatile content of several batches of adhesive were confirmed as being nominally 51%+/−1% and viscosity measurement was taken using a Brookfield RVT viscometer equipped with an appropriate spindle. Materials in heptane required a spindle number 3 while those in ethyl acetate required spindle number 5. The viscometer was set at 50 RPM for both readings. The viscosity of the materials in heptane was notably lower than those dissolved in ethyl acetate.

The rheological behavior of the dried multi-phase silicone acrylic hybrid visco-elastic compositions was also evaluated using a Rheometrics ARES rheometer. Between 2 and 3 grams of adhesive solution was poured onto a SCOTCH-PAK® 1022 fluoropolymer release liner and allowed to sit for 60 minutes under ambient conditions. To achieve essentially solvent-free films of the adhesive, they were placed in an oven at 110° C.+/−10° C. for 60 minutes. The films were removed from the oven and allowed to equilibrate to room temperature. The films were then removed from the release liner and folded over to form a square. These were compressed using a Carver press to eliminate air bubbles.

The rheometer was equipped with 8 mm plates and the gap zeroed. The sample was loaded between the plates and compressed. The rheometer's oven was heated to 30° C., and the samples were compressed to 1.5+/−0.1 mm. The excess adhesive was trimmed and the final gap recorded. A frequency sweep between 0.01 to 100 rad/s was performed w/the following settings: Temperature=30° C.; strain=0.5-1% and data collected at 3 points/decade. It was noted that there was a lower Eta* value in adhesives cast from heptane compared with those cast from ethyl acetate. The results are shown in Table 3.

TABLE 2

Appearance of Multi-Phase Silicone Acrylic Hybrid Visco-Elastic Compositions in Ethyl Acetate or Heptane as Second Solvent

| Sample No. | First Solvent | Silicone/ Acrylate Ratio | Acrylic Monomer Composition | Relative Tack | Second Solvent | Appearance |
|---|---|---|---|---|---|---|
| PSA 7 | Ethyl acetate | 50/50 | 50% 2-EHA/ 50% MA | Low | Heptane | Opaque, milky white |
| PSA 8 | Ethyl acetate | 50/50 | 50% 2-EHA/ 50% MA | Low | Ethyl Acetate | Opaque, light yellow color |
| PSA 9 | Heptane | 50/50 | 50% 2-EHA/ 50% MA | Low | Heptane | Opaque, milky white |
| PSA 10 | Heptane | 50/50 | 50% 2-EHA/ 50% MA | Low | Ethyl Acetate | Opaque, light yellow color |
| PSA 11 | Ethyl acetate | 50/50 | 60% 2-EHA/ 40% MA | High | Heptane | Opaque, milky white |
| PSA 12 | Ethyl acetate | 50/50 | 60% 2-EHA/ 40% MA | High | Ethyl Acetate | Opaque, light yellow color |
| PSA 13 | Heptane | 50/50 | 60% 2-EHA/ 40% MA | High | Heptane | Opaque, milky white |
| PSA 14 | Heptane | 50/50 | 60% 2-EHA/ 40% MA | High | Ethyl Acetate | Opaque, light yellow color |

TABLE 3

Volatile Content, Viscosity and Rheological Values of Silicone-Acrylic
Hybrid Pressure Sensitive Adhesive Solids Polymerized in Ethyl Acetate
or Heptane and Re-Dissolved in Ethyl Acetate or Heptane

| Sample No. | Replicate | First Solvent | Second Solvent | Relative Tack | Volatile Content (%) | Viscosity (cP) | Eta* @ 0.1 rad/s, 30 C. (P) | Eta* @ 0.01 rad/s, 30 C. (P) |
|---|---|---|---|---|---|---|---|---|
| PSA 7 | 1 | Ethyl acetate | Heptane | Low | 51.9 | 118 | 6.5E+07 | 2.0E+08 |
| PSA 8 | 1 | Ethyl acetate | Ethyl acetate | Low | 51.2 | 2832 | 4.7E+06 | 1.4E+07 |
| PSA 7 | 2 | Ethyl acetate | Heptane | Low | 50.6 | 74 | 2.8E+07 | 6.4E+07 |
| PSA 8 | 2 | Ethyl acetate | Ethyl acetate | Low | 50.1 | 2365 | 5.6E+06 | 1.5E+07 |
| PSA 11 | 1 | Ethyl acetate | Heptane | High | 50.5 | 294 | 2.1E+07 | 5.9E+07 |
| PSA 12 | 1 | Ethyl acetate | Ethyl acetate | High | 50.8 | 1696 | 2.2E+06 | 7.3E+06 |
| PSA 11 | 2 | Ethyl acetate | Heptane | High | 50.9 | 128 | 6.4E+06 | 1.7E+07 |
| PSA 12 | 2 | Ethyl acetate | Ethyl acetate | High | 50.5 | 1368 | 2.1E+06 | 4.4E+06 |
| PSA 9 | 1 | Heptane | Heptane | Low | 51.5 | 206 | 7.2E+07 | 2.2E+08 |
| PSA 10 | 1 | Heptane | Ethyl acetate | Low | 51.0 | 2520 | 7.5E+06 | 2.3E+07 |
| PSA 13 | 1 | Heptane | Heptane | High | 51.9 | 358 | 8.4E+07 | 2.6E+08 |
| PSA 14 | 1 | Heptane | Ethyl acetate | High | 51.3 | 2232 | 4.0E+06 | 1.3E+07 |

The differences in the phase arrangement of dried films of the multi-phase silicone acrylic hybrid visco-elastic compositions were confirmed via Transmission Electron Microscopy (TEM). In the TEM, silicone is shown as dark, while acrylate is light. Both high tack and low tack adhesives demonstrate similar phase arrangement, dependent upon the second solvent in which the adhesive is dispersed and cast from, with a silicone continuous phase and acrylate domains when the adhesive is dispersed in and cast from heptane and an acrylate continuous phase with silicone domains when the adhesive is dispersed in and cast from ethyl acetate. FIG. 1 shows a transmission electron micrograph of a high tack, hybrid visco-elastic polymer film dried from a multi-phase silicone acrylic hybrid visco-elastic composition polymerized in ethyl acetate and dispersed in heptane (a) and ethyl acetate (b) and a low tack hybrid visco-elastic polymer film dried from a multi-phase silicone acrylic hybrid visco-elastic composition polymerized in ethyl acetate and dispersed in heptane (c) and ethyl acetate (d). The light color in the micrographs corresponds to the acrylate phase and the dark color corresponds to the silicone phase.

Figure 2:
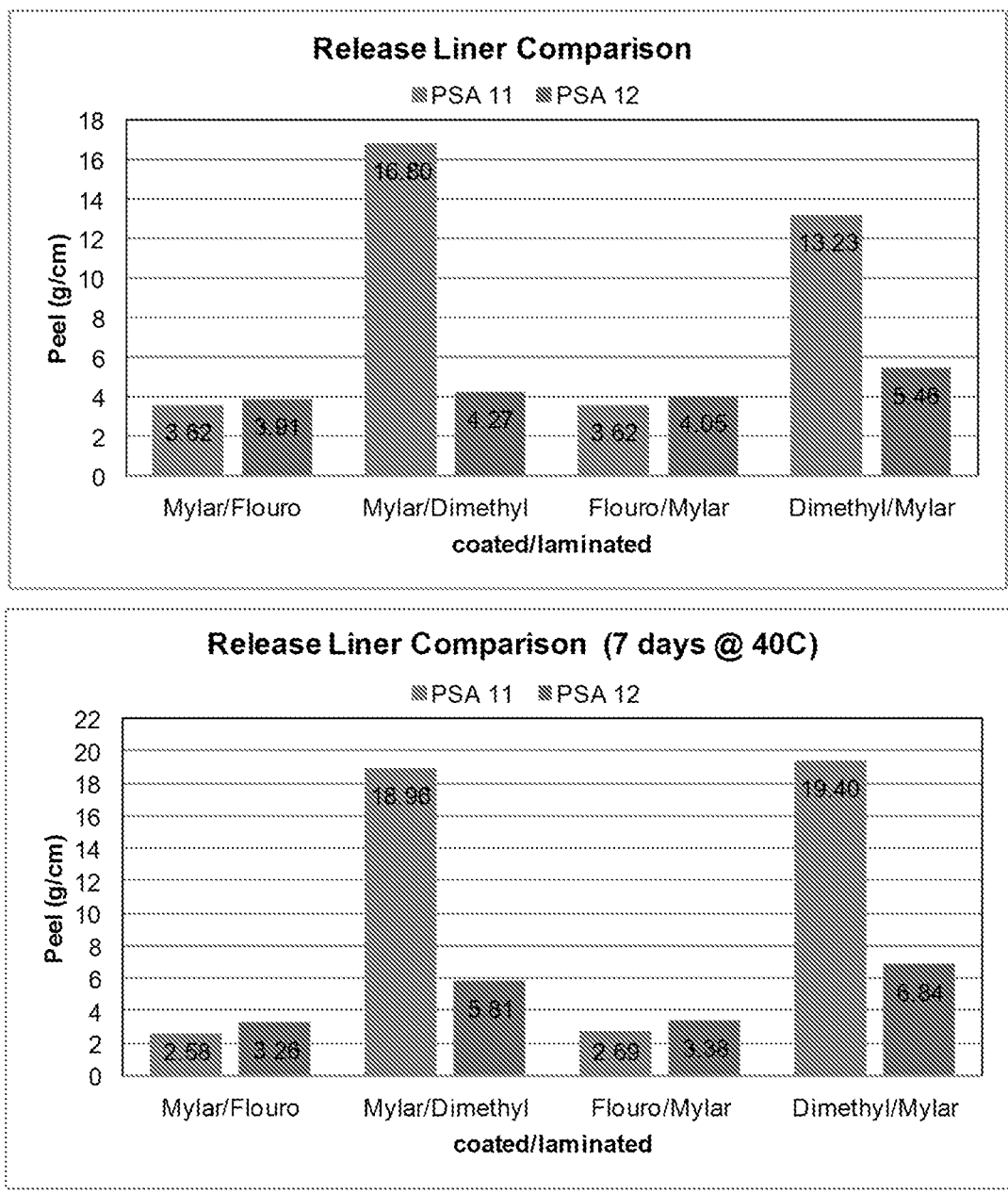
FIG. 2 shows peel release force from dimethylsilicone and fluorocarbon release liners of multi-phase silicone acrylic hybrid visco-elastic compositions cast from ethyl acetate or heptane solutions after storage at ambient and accelerated (7 days at 40° C.) conditions.

Example 8: Tape Properties of Multi-Phase Silicone Acrylic Hybrid Visco-Elastic Compositions Laminates were prepared by wet casting PSA 11 and PSA 12 onto a release liner (SCOTCH-PAK® 1022 or dimethylsilicone-based release liner), dried at 110° C. for 5 minutes, 1 mil dried thickness, laminated with 2 mil polyester film (Mylar) using 2 passes of a 2 kg roller. Laminates were also prepared by wet casting PSA 11 and PSA 12 onto 2 mil polyester film (Mylar), dried at 110° C. for 5 minutes, 1 mil dried thickness, laminated with release liner (SCOTCH-PAK® 1022 or dimethylsilicone-based release liner) using 2 passes of a 2 kg roller. The liner peel release force (1 inch wide strips) of laminates cast on two release liners was measured using an Instron Tensiometer. There was no observable difference with fluoropolymer liners between materials cast from ethyl acetate or heptane. There was a higher release force from dimethylsilicone (dimethyl) liner when cast from heptane. Furthermore, after aging the laminates for 7 days at 40° C., the release force differences between the adhesives cast from different solvents were even more pronounced. These results suggest that the adhesives retain a silicone external phase when cast from heptane and an acrylate external phase when cast from ethyl acetate initially and even after aging. FIG. 2 shows peel release force from dimethylsilicone and fluorocarbon release liners of multi-phase silicone acrylic hybrid visco-elastic compositions cast from ethyl acetate or heptane solutions after storage at ambient and accelerated (7 days at 40° C.) conditions.

Laminates were prepared by wet casting PSA 7-14 on SCOTCH-PAK® 1022 release liner to achieve a 1 mil (~25 micron) dried thickness. These were then transfer laminated onto 2 mil polyester films, and 2 passes of a 20 lb roller were used to ensure full lamination. After removal of the release liners, the adhesive and cohesive strength of the materials were measured.

The adhesive properties of 1 inch (2.54 cm) wide strips were measured against polished stainless steel using an Instron Tensiometer. Adhesive strips were adhered to the stainless steel panel using 2 passes with a 5 lb roller and allowed to dwell for 20 minutes prior to testing. The force to remove the adhesive from the stainless steel plate 180° peel at 12 in/min was measured and recorded.

Cohesive properties of the adhesives were measured using a 1-square inch adhesive laminate placed on a polished stainless steel adhered using 2 passes with a 5 lb roller. A 1 kg weight was suspended from the film and the time required to achieve cohesive failure as measured by the weight falling was recorded as the static shear.

It was discovered that adhesives with the same ratio of silicone-to-acrylate and 2-EHA:MA in the multi-phase silicone acrylic hybrid visco-elastic compositions may have different levels of appropriateness determined by the external phase (silicone or acrylate) of the material after casting and drying due to the solvent induced phase arrangement. For example, the cohesive strength of the materials cast from the two solvents indicated that adhesives cast from heptane exhibited a higher shear strength measurement (i.e. higher cohesive strength) than those cast from ethyl acetate due to the solvent induced phase arrangement. The higher cohesive strength observed with film cast from heptane translates into higher resistance to creep behavior and cold flow. Conversely the lower cohesive strength observed with film cast from ethyl acetate translates into higher softness and gentle skin adhesion. The peel adhesion and static shear measurements of the adhesives cast from heptane compared to those cast from ethyl acetate are shown in Table 4.

TABLE 4

Peel Adhesion and Static Shear Measurements of Hybrid Visco-Elastic Polymer Films Cast From Two Different Solvents

| Sample No. | Replicate | First Solvent | Second Solvent | Relative Tack | Peel Adhesion (N/10 mm) | Average Static Shear (min) |
|---|---|---|---|---|---|---|
| PSA 7 | 1 | Ethyl acetate | Heptane | Low | 484 | 13043 |
| PSA 8 | 1 | Ethyl acetate | Ethyl acetate | Low | 59 | 1330 |
| PSA 7 | 2 | Ethyl acetate | Heptane | Low | 588 | 3882 |
| PSA 8 | 2 | Ethyl acetate | Ethyl acetate | Low | 390 | 1018 |
| PSA 11 | 1 | Ethyl acetate | Heptane | High | 590 | 5291 |
| PSA 12 | 1 | Ethyl acetate | Ethyl acetate | High | 98 | 330 |
| PSA 11 | 2 | Ethyl acetate | Heptane | High | 432 | 188 |
| PSA 12 | 2 | Ethyl acetate | Ethyl acetate | High | 432 | 86 |
| PSA 9 | 1 | Heptane | Heptane | Low | 533 | >10000 |
| PSA 10 | 1 | Heptane | Ethyl acetate | Low | 577 | 1724 |
| PSA 13 | 1 | Heptane | Heptane | High | 522 | 9024 |
| PSA 14 | 1 | Heptane | Ethyl acetate | High | 1057 | 461 |

Example 9: Adhesive Wear Study #1

The ultimate utility of a medical adhesive is adhering to human skin. A study was conducted to determine how the multi-phase silicone acrylic hybrid visco-elastic compositions of the present invention would function adhering a patch to human skin. Two adhesives were selected for this study: a high tack hybrid adhesive (PSA 12) and a high tack silicone pressure sensitive adhesive. The silicone PSA selected as a comparative example was Dow Corning® BIO-PSA 7-4302 Pressure Sensitive Adhesive, a commercial, amine-compatible silicone adhesive in ethyl acetate available from Dow Corning Corp.

Patches were prepared by pouring approximately 10 grams of each adhesive on a 2-mil thick polyester substrate. A drawdown bar designed to provide a 3 mil thick coating was pulled towards the end of the laminate using constant speed and pressure until an even film was formed on the polyester substrate. The laminates were de-volatized at room temperature for 5 minutes and then placed in a forced-air oven at a 92° C. for 5 additional minutes. The laminates were removed from the oven and allowed to equilibrate at ambient temperature in the lab hood for a minimum of 16 hours before further processing.

The release liner (SCOTCH-PAK® 1022) was placed on the coated films. The release liner was affixed to the coated films using 2 passes of a 20-pound roller to ensure adequate lamination. Samples were trimmed to remove excess release liner. An adequate amount of circular patches with an area of 7.54 cm$^2$ for the study were prepared using an arch puncher. All samples were placed in Tower DualPeel® Self Seal Pouches, and the packages were labeled and sealed.

Four volunteers applied two patches to their upper arms. The volunteers were asked to provide a numerical score for the adhesion of each patch over a period of 7 days. The scoring system for adhesion of the patches is indicated below:

0=≥90% adhered (essentially no lift off the skin)
1=≥75% to <90% adhered (some edges only lifting off the skin)
2=≥50% to <75% adhered (less than half of the patch lifting off the skin)
3=>0% to <50% adhered but not detached (more than half of the patch lifting off the skin without falling off)
4=0% adhered-patch detached (patch completely off the skin)

Hence, a lower score indicates a patch that demonstrated more adhesion to skin.

The scores provided by the volunteers are provided in Tables 5 and 6. As can be seen, the number of respondents who rated the silicone patches (comparative example) a perfect zero, indicating ≥90% adhered (essentially no lift off the skin) throughout the study was lower than the hybrid which received perfect scores throughout the study. In fact, for the silicone PSA, two patches completely detached (one on Day 5 and a second on Day 6). The hybrid displayed a perfect score throughout the volunteer trial.

TABLE 5

Scores Provided for the Silicone Patch

| | Day | | | | | | | |
|---|---|---|---|---|---|---|---|---|
| Score | 1 | 2 | 3 | 4 | 5 | 6 | 7 | Total |
| 0 | 8 | 8 | 6 | 4 | 3 | 3 | 3 | 35 |
| 1 | 0 | 0 | 2 | 3 | 2 | 1 | 1 | 9 |
| 2 | 0 | 0 | 0 | 1 | 2 | 2 | 2 | 7 |
| 3 | 0 | 0 | 0 | 0 | 0 | 0 | 0 | 0 |
| 4 | 0 | 0 | 0 | 0 | 1 | 1 | 0 | 2 |
| | | | | | | | | 53 |

TABLE 6

Scores Provided for the Hybrid Visco-Elastic Polymer Film (PSA 12) Patch

| Score | \multicolumn{7}{c}{Day} | Total |
|---|---|---|---|---|---|---|---|---|
|  | 1 | 2 | 3 | 4 | 5 | 6 | 7 |  |
| 0 | 8 | 8 | 8 | 8 | 8 | 8 | 8 | 56 |
| 1 | 0 | 0 | 0 | 0 | 0 | 0 | 0 | 0 |
| 2 | 0 | 0 | 0 | 0 | 0 | 0 | 0 | 0 |
| 3 | 0 | 0 | 0 | 0 | 0 | 0 | 0 | 0 |
| 4 | 0 | 0 | 0 | 0 | 0 | 0 | 0 | 0 |
|  |  |  |  |  |  |  |  | 56 |

Example 10—Adhesive Wear Study #2

A second wear study was conducted to compare the wear time between the multi-phase silicone acrylic hybrid visco-elastic compositions cast out of ethyl acetate (PSA 12) and the same pressure sensitive solids cast out of heptane (PSA 11). Sample preparation was performed as in the first study of Example 9. A total of five volunteers applied two patches cast from ethyl acetate (PSA 12) and two cast from heptane (PSA 11). Circular patches with an area of 7.54 cm² were applied to their upper right or left arm for up to a total of 7 days (168 hours). To limit variability of applying the patch, the patches were applied by one designated person and the participant was blind to treatment. All other study parameters were the same as for the first wear study except for the addition of scoring cold flow as listed below. The scores provided by the volunteers are provided in Tables 7 and 8.

TABLE 7

Scores Provided for the Hybrid Visco-Elastic Polymer Film (PSA 11) Cast From Heptane

| Score | 1 | 2 | 3 | 4 | 5 | 6 | 7 | Total |
|---|---|---|---|---|---|---|---|---|
| 0 | 6 | 7 | 7 | 7 | 7 | 9 | 10 | 53 |
| 1 | 4 | 2 | 1 | 3 | 3 | 1 | 0 | 14 |
| 2 | 0 | 1 | 2 | 0 | 0 | 0 | 0 | 3 |
| 3 | 0 | 0 | 0 | 0 | 0 | 0 | 0 | 0 |
| 4 | 0 | 0 | 0 | 0 | 0 | 0 | 0 | 0 |
|  |  |  |  |  |  |  |  | 70 |

TABLE 8

Scores Provided for the Hybrid Visco-Elastic Polymer Film (PSA 12) Cast from Ethyl Acetate

| Score | 1 | 2 | 3 | 4 | 5 | 6 | 7 | Total |
|---|---|---|---|---|---|---|---|---|
| 0 | 8 | 10 | 10 | 10 | 10 | 10 | 10 | 68 |
| 1 | 1 | 0 | 0 | 0 | 0 | 0 | 0 | 1 |
| 2 | 0 | 0 | 0 | 0 | 0 | 0 | 0 | 0 |
| 3 | 0 | 0 | 0 | 0 | 0 | 0 | 0 | 0 |
| 4 | 1 | 0 | 0 | 0 | 0 | 0 | 0 | 1 |
|  |  |  |  |  |  |  |  | 70 |

Scoring of Cold Flow

Cold flow is the formation of a dark ring about the transdermal patch during use and signifies that the adhesive is oozing from the patch. Pictures were taken of the patches that experienced cold flow to aid in scoring. The scores for cold flow of the transdermal patch were as indicated below:

0=no cold flow observed
1=cold flow observed on patch (dark edges of patch)
2=cold flow observed on skin minimal <1 mm
3=cold flow observed on skin mm Cold flow was observed with both types of adhesive patches; however, it was subjectively rated as being less intense for the hybrid visco-elastic polymer film cast from heptane. The responses received from the volunteers are provided in Tables 9 and 10.

TABLE 9

Responses for Cold Flow in Hybrid Visco-Elastic Polymer Film (PSA 11) Cast From Heptane

| Score | 1 | 2 | 3 | 4 | 5 | 6 | 7 | Total |
|---|---|---|---|---|---|---|---|---|
| 0 | 10 | 8 | 8 | 8 | 6 | 6 | 6 | 52 |
| 1 | 0 | 2 | 2 | 2 | 4 | 4 | 4 | 18 |
| 2 | 0 | 0 | 0 | 0 | 0 | 0 | 0 | 0 |
| 3 | 0 | 0 | 0 | 0 | 0 | 0 | 0 | 0 |
|  |  |  |  |  |  |  |  | 70 |

TABLE 10

Responses for Cold Flow in Hybrid Visco-Elastic Polymer Film (PSA 12) Cast From Ethyl Acetate

| Score | 1 | 2 | 3 | 4 | 5 | 6 | 7 | Total |
|---|---|---|---|---|---|---|---|---|
| 0 | 8 | 6 | 2 | 0 | 0 | 0 | 0 | 16 |
| 1 | 0 | 1 | 5 | 5 | 6 | 6 | 5 | 28 |
| 2 | 2 | 2 | 2 | 4 | 3 | 3 | 4 | 20 |
| 3 | 0 | 0 | 0 | 0 | 0 | 0 | 0 | 0 |
|  |  |  |  |  |  |  |  | 64 |

When compared, the hybrid adhesive cast from ethyl acetate (PSA 12) and having an acrylate external phase had better adhesive (wear) properties when worn for 7 days than the adhesive cast from the heptane which had a silicone external phase. However, the hybrid adhesive cast from heptane (PSA 11, silicone external phase) exhibited less cold flow than the hybrid cast from ethyl acetate (PSA 12 acrylate external phase).

Example 11—Impact of Domain Arrangement on Solubility

Hansen solubility parameters provide a means to mathematically predict if one material will dissolve in another and form a solution. Predictions about which solvents will solubilize the hybrid solids in addition to heptane and ethyl acetate were made based on Hansen solubility parameters and are included in Table 11.

TABLE 11

Predicted Solubility in Additional Solvents

| Solvent | HSP Parameters | | | Predicted Solubility | | |
|---|---|---|---|---|---|---|
| | δD Dispersion | δP Polar | δH Hydrogen Bonding | Silicone Solubility | Acrylic Solubility (65:35 EHA:MA) | Hybrid Solids Solubility (65:35 EHA:MA) |
| Ethyl Acetate | 15.8 | 5.3 | 7.2 | good | good | good |
| Heptane | 15.3 | 0.0 | 0.0 | good | poor | good |
| Hexane | 14.9 | 0.0 | 0.0 | good | poor | poor |
| Cyclohexane | 16.8 | 0.0 | 0.2 | good | good | good |
| Toluene | 18 | 1.4 | 2 | good | good | good |
| Methyl Ethyl Ketone (MEK) | 16.0 | 9.0 | 5.1 | poor | good | good |
| Tetrahydrofuran (THF) | 16.8 | 5.7 | 8 | good | good | good |
| Isopropyl alcohol (IPA) | 15.8 | 6.1 | 16.4 | poor | good | poor |
| Cyclohexanone | 17.8 | 8.4 | 5.1 | poor | good | good |
| Hexamethyldisiloxane | 12.6 | 2.0 | 0.0 | good | poor | poor |
| Acetone | 15.5 | 10.4 | 7.0 | poor | good | good |
| Isododecane | 15.6 | 2.1 | 2.6 | good | good | good |
| Decamethylcyclopentasiloxane | 11.3 | 2.6 | 3.4 | good | poor | poor |
| Ethyl acetate/Heptane blend 1:1 | 15.6 | 2.7 | 3.6 | good | good | good |

These predicted solubilities were confirmed in the laboratory as shown in Table 12. Hansen solubility parameters were determined to be a good predictor of additional solvents and, therefore, allow the utility of other solvents beyond the ones used in the majority of the experiments. The measured solubility was performed on a "low tack" hybrid with a 50:50 EHA:MA ratio and dried from ethyl acetate (PSA 3, acrylate phase external), a "low tack" hybrid with a 50:50 EHA:MA ratio and dried from heptane (PSA 4, silicone phase external) and a "high tack" hybrid with a 60:40 EHA:MA ratio and dried from heptane (PSA 6, silicone phase external). This was performed by placing the hybrid solids in a jar along with an equal amount of solvent by weight and placing on a mixing wheel. These studies indicate that by controlling the phase arrangement through solvent selection, the solubility of the material can be manipulated and is primarily influenced by the external phase; for example, Table 11 indicates that heptane is a good solvent for silicone and a poor solvent for acrylate (65:35 EHA:MA) and the data in Table 12 confirms that when the silicone phase is external (as in PSA 4) the solubility in heptane is enhanced.

TABLE 12

Solubility in Various Solvents

| | Measured Solubility | | | | | |
|---|---|---|---|---|---|---|
| | PSA 3 - dried (First Solvent - Ethyl Acetate) | | PSA 4 - dried (First Solvent - Heptane) | | PSA 6 - dried (First Solvent - Heptane) | |
| Second Solvent | Comments | Time on Mixing Wheel | Comments | Time on Mixing Wheel | Comments | Time on Mixing Wheel |
| Ethyl Acetate | complete dissolution | 20 hrs | — | — | complete dissolution | <21 hrs |
| Heptane | nearly complete | 224 hrs | — | — | complete dissolution | 67 hrs |
| Hexane | incomplete | 296 hrs | — | — | complete dissolution | 67 hrs |
| Cyclohexane | nearly complete | 144 hrs | — | — | — | — |
| Toluene | incomplete | 196 hrs | complete dissolution | 24 hrs | — | — |
| Methyl Ethyl Ketone (MEK) | complete dissolution | 20 hrs | complete dissolution | <23 hrs | — | — |
| Tetrahydrofuran (THF) | complete dissolution | 24 hrs | — | — | — | — |
| Isopropyl alcohol (IPA) | incomplete | 296 hrs | complete dissolution (some phase separation) | 484 hrs | — | — |

TABLE 12-continued

Solubility in Various Solvents

Measured Solubility

| Second Solvent | PSA 3 - dried (First Solvent - Ethyl Acetate) Comments | Time on Mixing Wheel | PSA 4 - dried (First Solvent - Heptane) Comments | Time on Mixing Wheel | PSA 6 - dried (First Solvent - Heptane) Comments | Time on Mixing Wheel |
|---|---|---|---|---|---|---|
| Cyclohexanone | solvent completely absorbed | 180 hrs | complete dissolution | 171 hrs | — | — |
| Hexamethyldisiloxane | no solubility | 136 hrs | — | — | — | — |
| Acetone | solvent completely absorbed | 48 hrs | complete dissolution | <24 hrs | — | — |
| Isododecane | no solubility | 144 hrs | complete dissolution | 266 hrs | — | — |
| Decamethylcyclo-pentasiloxane | no solubility | 128 hrs | — | — | incomplete | 540 hrs |
| Ethyl acetate/Heptane blend 1:1 | complete dissolution | 16 hrs | — | — | — | — |

Table 12 Note:
no solubility - solvent was still clear;
incomplete - solvent became cloudy, but >10% solids remained;
nearly complete - <5% solids remained;
solvent completely absorbed - solids swelled but retained shape

Example 12: Domain Arrangement Controlled Through Blending

This example shows the impact on rheology by blending additional silicone resulting in a change in the domain orientation.

A silicone acrylate hybrid visco-elastic composition was prepared in ethyl acetate with 48.8% acrylate composed of 50:50 2EHA:MA as previously described in Example 3. After complete removal of the solvent (forced-air oven, 100° C. for 24 hrs), the hybrid was dispersed in both ethyl acetate (50.6% non-volatile content) and heptane (49.7% non-volatile content). To each of these solvated hybrid compositions, additional silicone PSA was added to provide a range of acrylate ratios from 0-48.8 wt. % along with additional solvent to achieve 50 wt. % non-volatile content for all samples (see Table 13). After mixing overnight, the samples were dried on a release liner to remove all solvent. The dried samples were tested on a TA ARES rheometer equipped with 8 mm stainless steel parallel plates. The samples were compressed to 1.5+/−0.1 mm and trimmed. The frequency sweeps were conducted at 30° C. with a 0.5% strain from 0.1 to 100 rad/s and 5 pts/decade.

TABLE 13

Blends of Silicone Acrylate Hybrid and Silicon-Containing Pressure Sensitive Adhesive Composition

| Sample No. | Acrylate (wt. %) | Silicone PSA in heptane (g) | Silicone PSA in ethyl acetate (g) | Hybrid in heptane (g) | Hybrid in ethyl acetate (g) | Ethyl acetate (g) | Heptane (g) |
|---|---|---|---|---|---|---|---|
| 12-1 | 0.0 | — | 8.415 | — | — | 1.583 | — |
| 12-2 | 5.0 | — | 7.559 | — | 1.019 | 1.432 | — |
| 12-3 | 10.2 | — | 6.691 | — | 2.063 | 1.290 | — |
| 12-4 | 15.0 | — | 5.834 | — | 3.045 | 1.158 | — |
| 12-5 | 20.0 | — | 4.990 | — | 4.063 | 0.993 | — |
| 12-6 | 22.0 | — | 4.626 | — | 4.469 | 0.922 | — |
| 12-7 | 24.1 | — | 4.288 | — | 4.921 | 0.873 | — |
| 12-8 | 30.0 | — | 3.245 | — | 6.072 | 0.683 | — |
| 12-9 | 40.0 | — | 1.519 | — | 8.122 | 0.384 | — |
| 12-10 | 48.8 | — | — | — | 10.000 | — | — |
| 12-11 | 0.0 | 8.429 | — | — | — | — | 1.582 |
| 12-12 | 4.2 | 7.560 | — | 1.013 | — | — | 1.433 |
| 12-13 | 8.6 | 6.700 | — | 2.028 | — | — | 1.230 |
| 12-14 | 13.3 | 5.828 | — | 3.062 | — | — | 1.135 |
| 12-15 | 17.9 | 4.966 | — | 4.050 | — | — | 0.982 |
| 12-16 | 27.8 | 3.257 | — | 6.092 | — | — | 0.687 |
| 12-17 | 38.6 | 1.527 | — | 8.133 | — | — | 0.381 |
| 12-18 | 48.8 | — | — | 10.000 | — | — | — |

Figure 3:
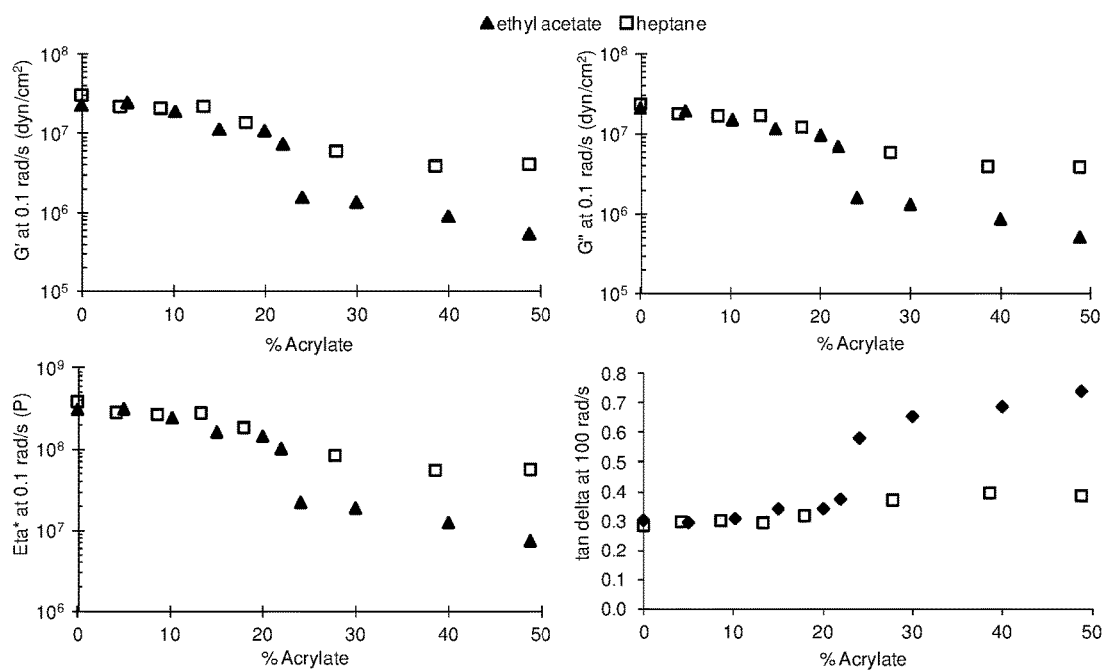
FIG. 3 shows the visco-elastic properties of blends of silicone acrylic hybrid compositions and silicon-containing pressure sensitive adhesive compositions blended to provide a range of acrylate contents. The figure shows blends prepared in both ethyl acetate and heptane.

The data points at 48.8% acrylate (samples 12-10 and 12-18) in FIG. 3 correspond to this hybrid dispersed in ethyl acetate and heptane (no silicone PSA blended in), which showed low and high modulus respectively. The data points at 0% acrylate (samples 12-1 and 12-11) correspond to the silicone PSA that was used to blend with the hybrid compositions. For the samples dried from heptane, the silicone was the external continuous phase throughout the entire range of acrylate concentrations; however, the modulus and complex viscosity steadily increased as the acrylate content was decreased. For the samples dried from ethyl acetate, the acrylate was the external continuous phase starting at 48.8% acrylate. However, as the acrylate content was decreased, the modulus and complex viscosity slowly increased until the acrylate content reached ~22-24 wt. %, at which point the phases inverted and the silicone became the external continuous phase. At this point, the rheology data of the materials dried from ethyl acetate dispersions and heptane dispersions overlaid.

Example 13: Ibuprofen Release

This example shows the impact on ibuprofen release by blending additional silicone resulting in a change in the domain orientation.

A silicone acrylate hybrid visco-elastic composition (referred to as hybrid) was prepared in ethyl acetate with 48.8% acrylate composed of 50:50 2EHA:MA as previously described in Example 3. After complete removal of the solvent (forced-air oven, 100° C. for 24 hrs), the hybrid was dispersed in ethyl acetate (50.6% non-volatile content). To these solvated hybrid compositions, additional silicone PSA was added to provide a range of acrylate ratios from 5-40 wt. % along with additional solvent to achieve 50 wt. % non-volatile content for all samples and 2.5 wt. % ibuprofen (see Table 14). After blending overnight, the adhesives were coated onto a fluoropolymer release liner and dried 70° C. for 15 minutes to remove the solvent. After drying, the adhesives were transfer laminated to 2 mil Mylar; the final coat weights were 7.0±0.5 mg/cm$^2$.

TABLE 14

Ibuprofen Formulations

| Sample No. | Acrylate (wt. %) | Silicone PSA in Ethyl Acetate (g) | Hybrid in Ethyl Acetate (g) | Ethyl Acetate (g) | 2.5% Ibuprofen (g) |
|---|---|---|---|---|---|
| 13-1 | 5.1 | 7.556 | 1.028 | 1.307 | 0.128 |
| 13-2 | 10.7 | 6.698 | 2.209 | 1.153 | 0.128 |
| 13-3 | 15.0 | 5.824 | 3.031 | 1.006 | 0.128 |
| 13-4 | 20.0 | 4.968 | 4.046 | 0.856 | 0.128 |
| 13-5 | 25.0 | 4.109 | 5.064 | 0.707 | 0.128 |
| 13-6 | 29.9 | 3.266 | 6.090 | 0.552 | 0.128 |
| 13-7 | 35.1 | 2.379 | 7.132 | 0.405 | 0.128 |
| 13-8 | 40.0 | 1.514 | 8.132 | 0.257 | 0.128 |

Patches were punched from each formulation laminate using a 7/16" punch. The release liners were removed and the patches were adhered to a larger sheet of release liner. Over-laminates were punched using a 1" punch from a sheet of Dow Corning® BIO-PSA 7-4302 coated on 2 mil Mylar (with a 2-3 mil applicator). The release liner was removed from the over-laminate and the over-laminate was placed on top of the patch, keeping the patch centered. The over-laminates with the adhered patches were then transferred to a Franz diffusion cell (~5 mL, 0.636 cm$^2$ permeation area) which were prefilled with ~3 mL of receptor fluid. After adhering the patches to the cells, the donor caps were capped in place and the cells were filled to full volume with receptor fluid. The start of the experiment was recorded at the filling of each cell (1 min staggering was used between cells to accommodate for time needed to sample and refill). The cells were magnetically stirred and maintained at 32° C. using a Logan manual Franz diffusion apparatus. For this study, 1 mL partial replacement was performed at 0.5, 1, 1.5, 2, 4 and 6 hours using phosphate buffered saline (PBS) pH 7.4.

Figure 4:
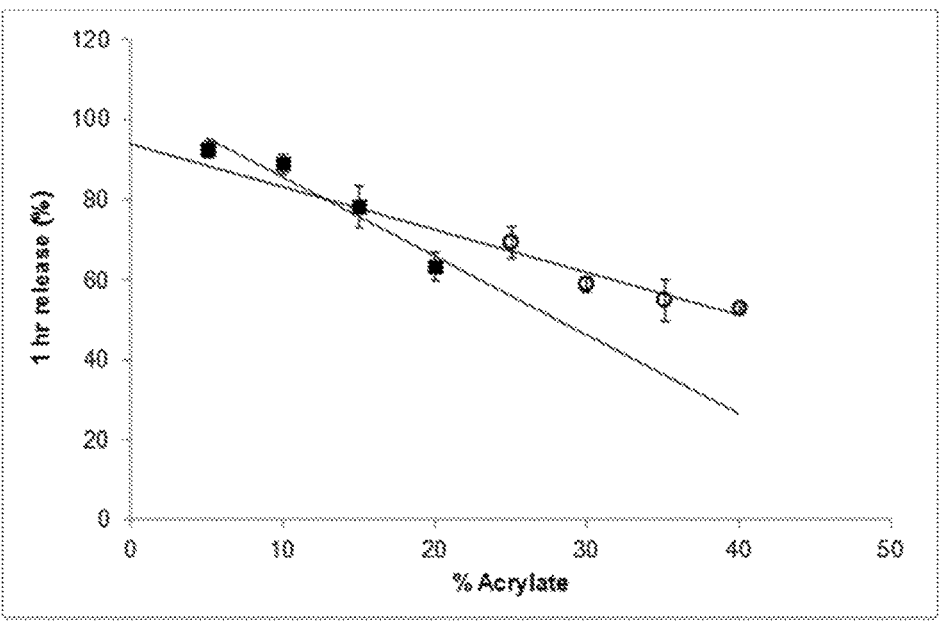
FIG. 4 shows the percent release of ibuprofen at 1 hr from patches prepared at 2.5 wt. % ibuprofen in blends of silicone acrylic hybrid compositions and silicon-containing pressure sensitive adhesive compositions to provide a range of acrylate contents.

The results (FIG. 4) show that the amount of ibuprofen released after 1 hr decreased as the wt. % acrylate in the patch was increased. However, there was a deviation in the slope between 20-25 wt. % acrylate, which was the range of wt. % acrylate that corresponded to the change in observed rheology (shown in Example 12) properties as a result of phase inversion. These results suggest that the drug delivery from these silicone acrylate hybrid visco-elastic compositions can be adjusted or tuned by manipulating the phase arrangement of the hybrid material.

Example 14: Estradiol Release

This example shows the impact on estradiol release by blending additional silicone resulting in a change in the domain orientation.

A silicone acrylate hybrid visco-elastic composition (referred to as hybrid) was prepared in ethyl acetate with 48.8% acrylate composed of 50:50 2EHA:MA as previously described in Example 3. After complete removal of the solvent (forced-air oven, 100° C. for 24 hrs), the hybrid was dispersed in ethyl acetate (50.6% non-volatile content). To these solvated hybrid compositions, additional silicone PSA was added to provide a range of acrylate ratios from 5-40 wt. % along with additional solvent to achieve 50 wt. % non-volatile content for all samples and 1.0 wt. % estradiol (see Table 15). After blending overnight, the adhesives were coated onto a fluoropolymer release liner and dried 92° C. for 5 minutes to remove the solvent. After drying, the adhesives were transfer laminated to 2 mil Mylar; the final coat weights were 6.6±0.7 mg/cm$^2$.

TABLE 15

Estradiol Formulations

| Sample No. | Acrylate (wt. %) | Silicone PSA in Ethyl Acetate (g) | Hybrid in Ethyl Acetate (g) | Ethyl Acetate (g) | 1.0% Estradiol (g) |
|---|---|---|---|---|---|
| 14-1 | 5.1 | 7.555 | 1.025 | 1.382 | 0.051 |
| 14-2 | 10.1 | 6.692 | 2.047 | 1.235 | 0.051 |
| 14-3 | 15.9 | 5.832 | 3.316 | 1.081 | 0.050 |
| 14-4 | 20.0 | 4.975 | 4.069 | 0.938 | 0.051 |
| 14-5 | 25.0 | 4.116 | 5.064 | 0.804 | 0.051 |
| 14-6 | 30.0 | 3.240 | 6.086 | 0.632 | 0.051 |
| 14-7 | 35.0 | 2.378 | 7.093 | 0.489 | 0.050 |
| 14-8 | 40.0 | 1.519 | 8.115 | 0.333 | 0.051 |

Patches were punched from each formulation laminate using a 7/16" punch. The release liners were removed and the patches were adhered to a larger sheet of release liner. Over-laminates were punched using a 1" punch from a sheet of Dow Corning® BIO-PSA 7-4302 coated on 2 mil Mylar (with a 2-3 mil applicator). The release liner was removed from the over-laminate and the over-laminate was placed on top of the patch, keeping the patch centered. The over-laminates with the adhered patches were then transferred to the Franz diffusion cell (~5 mL, 0.636 cm² permeation area) which were prefilled with ~3 mL of receptor fluid. After adhering the patches to the cells, the donor caps were capped in place and the cells were filled to full volume with receptor fluid. The start of the experiment was recorded at the filling of each cell (1 min staggering was used between cells to accommodate for time needed to sample and refill). The cells were magnetically stirred and maintained at 32° C. using a Logan manual Franz diffusion apparatus. For this study, 3 mL partial replacement was performed at 0.5, 1, 1.5, 2, 4 and 6 hours using 40% v/v PEG-400 in deionized water.

Figure 5:
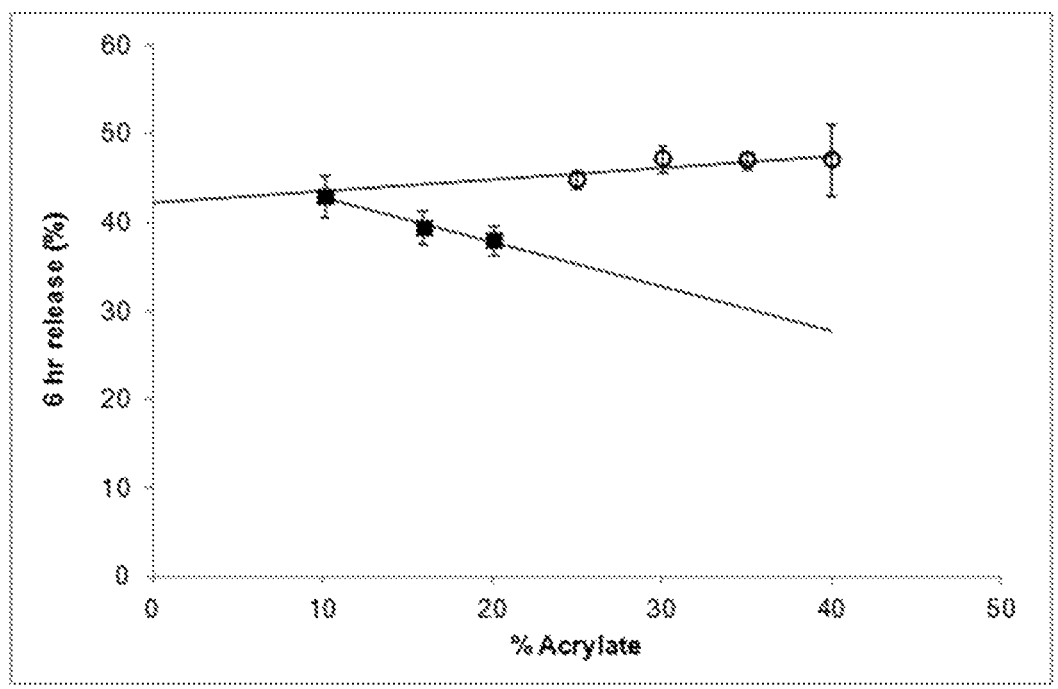
FIG. 5 shows the percent release of estradiol at 6 hr from patches prepared at 1 wt. % estradiol in blends of silicone acrylic hybrid compositions and silicon-containing pressure sensitive adhesive compositions to provide a range of acrylate contents.

These results show (FIG. 5) that the amount of estradiol released after 6 hr decreased as the wt. % acrylate in the patch was increased until between 20-25 wt. % acrylate, which was the range of wt. % acrylate that corresponded to the change in observed rheology properties (shown in Example 12) as a result of phase inversion. At this point, the amount release actual increased and remained essentially constant with increasing acrylate content. These results suggest that the drug delivery from these silicone acrylate hybrid visco-elastic compositions can be adjusted or tuned by manipulating the phase arrangement of the hybrid material. The estradiol crystallized in sample 14-1 resulting in very low release and, therefore, is not shown in FIG. 5.

Example 15: Lidocaine Release

This example shows the impact on lidocaine release by blending additional silicone resulting in a change in the domain orientation.

A silicone acrylate hybrid visco-elastic composition (referred to as hybrid) was prepared in ethyl acetate with 48.8% acrylate composed of 50:50 2EHA:MA as previously described in Example 3. After complete removal of the solvent (forced-air oven, 100° C. for 24 hrs), the hybrid was dispersed in ethyl acetate (50.6% non-volatile content). To these solvated hybrid compositions, additional silicone PSA was added to provide a range of acrylate ratios from 5-40 wt. % along with additional solvent to achieve 50 wt. % non-volatile content for all samples and 2.5 wt. % lidocaine (see Table 16). After blending overnight, the adhesives were coated onto a fluoropolymer release liner and dried 70° C. for 15 minutes to remove the solvent. After drying, the adhesives were transfer laminated to 2 mil Mylar; the final coat weights were 10.9±0.5 mg/cm2.

TABLE 16

Lidocaine Formulations

| Sample No. | Acrylate (wt. %) | Silicone PSA in Ethyl Acetate (g) | Hybrid in Ethyl Acetate (g) | Ethyl Acetate (g) | 2.5% Lidocaine (g) |
| --- | --- | --- | --- | --- | --- |
| 15-1 | 5.2 | 7.557 | 1.062 | 1.303 | 0.128 |
| 15-2 | 9.7 | 6.952 | 2.034 | 1.151 | 0.128 |
| 15-3 | 15.1 | 5.841 | 3.079 | 1.020 | 0.128 |
| 15-4 | 20.0 | 4.975 | 4.048 | 0.851 | 0.128 |
| 15-5 | 25.0 | 4.115 | 5.061 | 0.700 | 0.128 |
| 15-6 | 30.0 | 3.245 | 6.070 | 0.553 | 0.128 |
| 15-7 | 35.0 | 2.380 | 7.083 | 0.405 | 0.128 |
| 15-8 | 40.0 | 1.520 | 8.137 | 0.253 | 0.128 |

Patches were punched from each formulation laminate using a 7/16" punch. The release liners were removed and the patches were adhered to a larger sheet of release liner. Over-laminates were punched using a 1" punch from a sheet of Dow Corning® BIO-PSA 7-4302 coated on 2 mil Mylar (with a 2-3 mil applicator). The release liner was removed from the over-laminate and the over-laminate was placed on top of the patch, keeping the patch centered. The over-laminates with the adhered patches were then transferred to the Franz diffusion cell (~5 mL, 0.636 cm² permeation area) which were prefilled with ~3 mL of receptor fluid. After adhering the patches to the cells, the donor caps were capped in place and the cells were filled to full volume with receptor fluid. The start of the experiment was recorded at the filling of each cell (1 min staggering was used between cells to accommodate for time needed to sample and refill). The cells were magnetically stirred and maintained at 32° C. using a Logan manual Franz diffusion apparatus. For this study, 1 mL partial replacement was performed at 0.5, 1, 1.5, 2, 4 and 6 hours using PBS pH 7.4.

Figure 6:
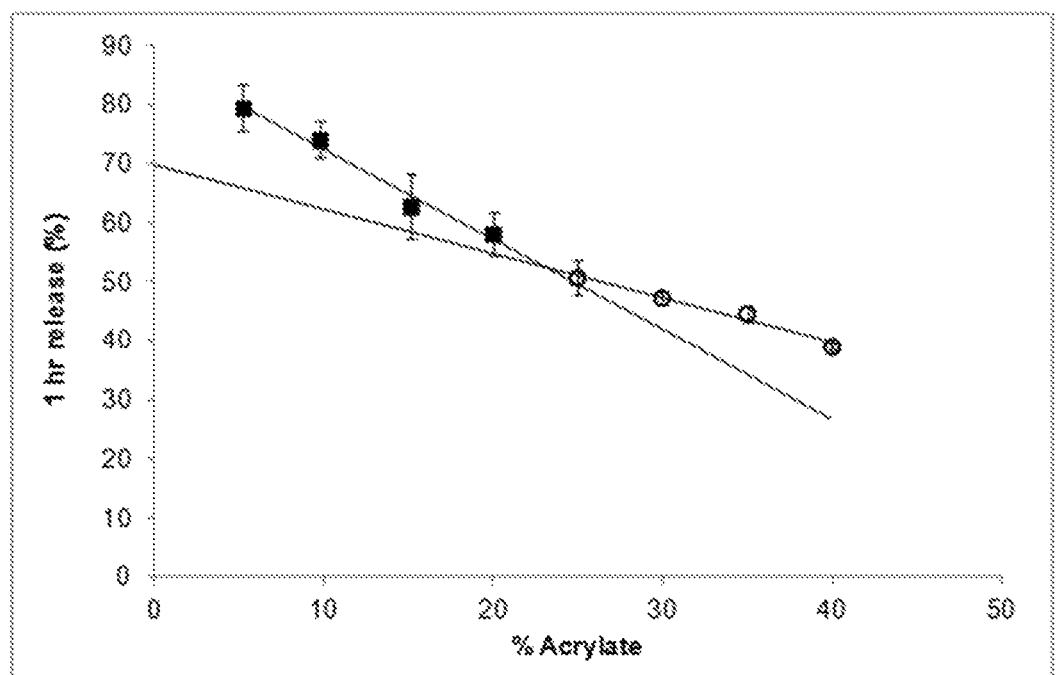
FIG. 6 shows the percent release of lidocaine at 1 hr from patches prepared at 2.5 wt. % lidocaine in blends of silicone acrylic hybrid compositions and silicon-containing pressure sensitive adhesive compositions to provide a range of acrylate contents.

The results show (FIG. 6) that the amount of lidocaine released after 1 hr decreased as the wt. % acrylate in the patch was increased. However, there was a deviation in the slope between 20-25 wt. % acrylate, which was the range of wt. % acrylate that corresponded to the change in observed rheology properties (shown in Example 12) as a result of phase inversion. These results suggest that the drug delivery from these silicone acrylate hybrid visco-elastic compositions can be adjusted or tuned by manipulating the phase arrangement of the hybrid material.

Example 16: Solvent Exchange

PSA 8 was diluted to 42% solids with addition of ethyl acetate. From this, approximately 371 g was added to a 500 mL 3-neck round-bottom flask equipped with an overhead mixer, a Dean-Stark trap, condenser and a solvent feed line. Dry N2 was used to blanket the reactor which was heated in an oil bath set at 115° C. The solution was heated under constant agitation and approximately 149 g of ethyl acetate was removed to yield an approximately 70% NVC. To this, approximately 86 g n-heptane was added to the reactor through the feed line using a pump. After addition of the second solvent, stripping was resumed and approximately 105 g of solvent was removed to yield an approximately 78% NVC.

After the solvent exchange, the solvent was completely removed (forced-air oven, 100° C. for 24 hr) to test the impact of the phase inversion on the solubility. As a comparative example, PSA 8 was also dried to remove the solvent.

After drying solids were placed into separate jars and n-heptane was added to make a 60% NVC. The jars were placed on the mixing wheel to disperse.

TABLE 17

Solvent Exchange Results

| Sample | Solids Wt. (g) | n-heptane Wt. (g) | Dissolution |
| --- | --- | --- | --- |
| PSA 8 (dried) | 22.74 | 15.16 | Incomplete - 216 hr |
| PSA 8 solvent exchanged to heptane and dried | 21.07 | 14.06 | Complete dissolution - 24 hr |

This example shows that solvent exchanging from ethyl acetate to heptane facilitates control of the phase arrangement resulting in a silicone external phase when the heptane is removed. By doing this, it is much easier to disperse the material into another solvent that the silicone phase has greater solubility in than the acrylate phase.

While the invention is susceptible to various modifications and alternative forms, specific embodiments have been shown by way of example in the drawings and described in detail herein. It should be understood, however, that the invention is not intended to be limited to the particular forms disclosed. Rather, the invention is to cover all modifications, equivalents, and alternatives falling within the spirit and scope of the invention as defined by the appended claims.

What is claimed is:

1. A method of making a multi-phase silicone acrylic hybrid visco-elastic composition comprising the steps of:
   (i) providing a silicon-containing pressure sensitive adhesive composition comprising acrylate or methacrylate functionality and the condensation reaction product of:
      a silicone resin,
      a silicone polymer, and
      a silicon-containing capping agent which provides said acrylate or methacrylate functionality, wherein said silicon-containing capping agent is of the general formula $XYR'_bSiZ_{3-b}$, wherein
      X is a monovalent radical of the general formula AE—
      where E is —O— or —NH— and A is an acryl group or a methacryl group,
      Y is a divalent alkylene radical having from 1 to 6 carbon atoms,
      R' is a methyl or a phenyl radical,
      Z is a monovalent hydrolyzable organic radical or a halogen, and
      b is 1, or 2;
      wherein the silicone resin and silicone polymer are reacted to form a pressure sensitive adhesive, wherein the silicon-containing capping agent is introduced prior to, during, or after the silicone resin and silicone polymer are reacted, and wherein:
         the silicon-containing capping agent reacts with the pressure sensitive adhesive after the silicone resin and silicone polymer have been condensation reacted to form the pressure sensitive adhesive; or
         the silicon-containing capping agent reacts in-situ with the silicone resin and silicone polymer;
   (ii) polymerizing an ethylenically unsaturated monomer and the silicon-containing pressure sensitive adhesive composition of step (i) in a first solvent in the presence of an initiator at a temperature of from 50° C. to 100° C. to form a silicone acrylic hybrid composition;
   (iii) removing the first solvent; and
   (iv) adding a second solvent to form the multi-phase silicone acrylic hybrid visco-elastic composition, wherein the phase arrangement of the multi-phase silicone acrylic hybrid visco-elastic composition is selectively controlled by selection of the second solvent.

2. A method of making a multi-phase silicone acrylic hybrid visco-elastic composition comprising the steps of:
   (i) providing a silicon-containing pressure sensitive adhesive composition comprising acrylate or methacrylate functionality and the condensation reaction product of:
      a silicone resin,
      a silicone polymer, and
      a silicon-containing capping agent which provides said acrylate or methacrylate functionality, wherein said silicon-containing capping agent is of the general formula $XYR'_bSiZ_{3-b}$, wherein
      X is a monovalent radical of the general formula AE—
      where E is —O— or —NH— and A is an acryl group or a methacryl group,
      Y is a divalent alkylene radical having from 1 to 6 carbon atoms,
      R' is a methyl or a phenyl radical,
      Z is a monovalent hydrolyzable organic radical or a halogen, and
      b is 0, 1 or 2;
      wherein the silicone resin and silicone polymer are reacted to form a pressure sensitive adhesive, wherein the silicon-containing capping agent is introduced prior to, during, or after the silicone resin and silicone polymer are reacted, and wherein:
         the silicon-containing capping agent reacts with the pressure sensitive adhesive after the silicone resin and silicone polymer have been condensation reacted to form the pressure sensitive adhesive; or
         the silicon-containing capping agent reacts in-situ with the silicone resin and silicone polymer;
   (ii) polymerizing an ethylenically unsaturated monomer and the silicon-containing pressure sensitive adhesive composition of step (i) in a first solvent in the presence of an initiator at a temperature of from 50° C. to 100° C. to form a silicone acrylic hybrid composition;
   (iii) adding a processing solvent, wherein the processing solvent has a higher boiling point than the first solvent, and
   (iv) applying heat at a temperature of from 70° C. to 150° C. such that a majority of the first solvent is selectively removed;
   (v) removing the processing solvent; and
   (vi) adding a second solvent to form the multi-phase silicone acrylic hybrid visco-elastic composition, wherein the phase arrangement of the multi-phase silicone acrylic hybrid visco-elastic composition is selectively controlled by selection of the second solvent.

3. The method of claim 1 or claim 2, further including the step of blending the silicone acrylic hybrid composition from step (ii) with a non-hybrid pressure sensitive adhesive composition prior to step (iii), wherein the phase arrangement of the multi-phase silicone acrylic hybrid visco-elastic composition is selectively controlled by the blending step.

4. The method of claim 1, further including the step of blending the multi-phase silicone acrylic hybrid visco-elastic composition with a non-hybrid pressure sensitive adhesive composition after step (iv), wherein the phase arrangement of the multi-phase silicone acrylic hybrid visco-elastic composition is selectively controlled by the blending step.

5. The method of claim 2, further including the step of blending the multi-phase silicone acrylic hybrid visco-elastic composition with a non-hybrid pressure sensitive adhesive composition after step (vi), wherein the phase arrangement of the multi-phase silicone acrylic hybrid visco-elastic composition is selectively controlled by the blending step.

6. The method of claim 1 or claim 2, wherein the resulting multi-phase silicone acrylic hybrid visco-elastic composition contains a continuous, silicone external phase and a discontinuous, acrylic internal phase as selectively controlled by selection of the second solvent.

7. The method of claim 1 or claim 2, wherein the resulting multi-phase silicone acrylic hybrid visco-elastic composition contains a continuous, acrylic external phase and a discontinuous, silicone internal phase as selectively controlled by selection of the second solvent.

8. The method of claim 1 or claim 2, wherein the second solvent is selected from a volatile silicone, an aliphatic solvent, an aromatic solvent, a ketone, an ester, a halogenated solvent, a mineral spirit, and combinations thereof.

9. The method of claim 1 or claim 2, wherein where the second solvent is heptane, the multi-phase silicone acrylic hybrid visco-elastic composition contains a silicone external phase.

10. The method of claim 1 or claim 2, wherein where the second solvent is ethyl acetate, the multi-phase silicone acrylic hybrid visco-elastic composition contains an acrylate external phase.

11. A multi-phase silicone acrylic hybrid visco-elastic composition formed by the method of claim 1 or 2.

12. A multi-phase silicone acrylic hybrid visco-elastic composition formed by the methods of claim 1 or 2, wherein the ratio of silicone to acrylate is from 5 to 95 parts silicone to 95 to 5 parts acrylate to selectively control the phase arrangement of the multi-phase silicone acrylic hybrid visco-elastic composition.

13. A visco-elastic polymer film formed by a method of applying the multi-phase silicone acrylic hybrid visco-elastic composition formed by the methods of claim 1 or 2 to a substrate and subsequently removing the second solvent.

14. A transdermal drug delivery system comprising the visco-elastic polymer film of claim 13.

15. A transdermal drug delivery system comprising at least one active and the multi-phase silicone acrylic hybrid visco-elastic composition formed by the method of claim 1 or 2, wherein release of an active from the transdermal drug delivery system is capable of being tuned by selectively controlling the phase arrangement of the multi-phase silicone acrylic hybrid visco-elastic composition.

16. The visco-elastic polymer film of claim 13, wherein the multi-phase silicone acrylic hybrid visco-elastic composition allows the control and adjustment of the physical and solubility properties of the visco-elastic polymer film when used in a transdermal drug delivery system, a pressure sensitive adhesive film, film former or a medical device attachment.

17. A pressure sensitive adhesive film comprising the visco-elastic polymer film of claim 13.

18. A medical device attachment comprising the visco-elastic polymer film of claim 13.

* * * * *